United States Patent [19]

Ohnishi et al.

[11] Patent Number: 4,840,945
[45] Date of Patent: Jun. 20, 1989

[54] CEPHALOSPORIN DERIVATIVES

[75] Inventors: Haruo Ohnishi, Funabashi; Hiroshi Kosuzume, Mishima; Masahiro Mizota, Gotenba; Yasuo Suzuki, Kawaguchi; Ei Mochida, Toshima, all of Japan

[73] Assignee: Mochida Pharmaceutical Co., Ltd., Tokyo, Japan

[21] Appl. No.: 838,309

[22] Filed: Mar. 10, 1986

[30] Foreign Application Priority Data

| | | |
|---|---|---|
| Apr. 1, 1985 [JP] | Japan | 60-68866 |
| May 17, 1985 [JP] | Japan | 60-105704 |
| Jul. 4, 1985 [JP] | Japan | 60-147359 |
| Jul. 27, 1985 [JP] | Japan | 60-166259 |

[51] Int. Cl.$^4$ .................. C07D 501/36; A61K 31/545
[52] U.S. Cl. .................................... 514/206; 540/227; 540/226
[58] Field of Search ............................... 544/229, 227

[56] References Cited

U.S. PATENT DOCUMENTS

| | | | |
|---|---|---|---|
| 4,103,085 | 7/1978 | Naito et al. | 544/27 |
| 4,104,469 | 8/1978 | Naito et al. | 544/27 |
| 4,151,352 | 4/1979 | Naito et al. | 544/26 |
| 4,278,793 | 7/1981 | Durckheimer et al. | 544/27 |
| 4,316,024 | 2/1982 | Iimura et al. | 548/27 |
| 4,331,666 | 5/1982 | Nannini et al. | |
| 4,436,912 | 3/1984 | Wheeler | 548/233 |
| 4,500,526 | 2/1985 | Imae et al. | 514/226 |
| 4,526,977 | 7/1985 | Commons et al. | 548/246 |
| 4,547,494 | 10/1985 | Oine et al. | 514/204 |
| 4,576,956 | 3/1986 | Makisumi | 514/380 |
| 4,587,333 | 5/1986 | Ono et al. | 544/521 |
| 4,594,417 | 6/1986 | Yang | 544/28 |
| 4,600,773 | 7/1986 | Engel | 544/30 |
| 4,604,457 | 8/1986 | Torii et al. | 540/223 |
| 4,609,654 | 9/1986 | Labeew et al. | 540/227 |
| 4,621,081 | 11/1986 | O'Callaghan et al. | 540/227 |

FOREIGN PATENT DOCUMENTS

| | | |
|---|---|---|
| 0075805 | 6/1983 | European Pat. Off. |
| 0150507 | 8/1985 | European Pat. Off. |
| 2128498 | 12/1971 | Fed. Rep. of Germany |
| 2456109 | 12/1980 | France |
| 60-142987 | 7/1985 | Japan |
| 189245 | 1/1977 | New Zealand |
| 203436 | 6/1980 | New Zealand |
| 186968 | 4/1981 | New Zealand |
| 188163 | 10/1981 | New Zealand |
| 196642 | 7/1984 | New Zealand |
| 202332 | 10/1985 | New Zealand |
| 206704 | 4/1986 | New Zealand |
| 893428 | 4/1962 | United Kingdom |
| 1399086 | 6/1975 | United Kingdom |
| 2017702 | 10/1979 | United Kingdom |
| 1576625 | 10/1980 | United Kingdom |
| 1604971 | 12/1981 | United Kingdom |
| 2104888 | 3/1983 | United Kingdom |

OTHER PUBLICATIONS

Chemical Abstracts, vol. 99, 1983, Abstract No. 87919x.
Chemical Abstracts, vol. 100, 1984, Abstract No. 22505d.
Chemical Abstracts, vol. 102, 1985, Abstract No. 6056u.
Chemical Abstracts, vol. 102, 1985, Abstract No. 24359z.
Chemical Abstracts, vol. 103, 1985, Abstract No. 37281p.
Naito et al., "Cephalosporins III," 30 Journal of Antibiotics 705 (9/77).
Dunn, J. Antimicrob Chemotheraph (1982) 10 Suppl. C pp. 1–10.
Alpegian et al., Cephalosporins VI, 36 J. Antibiotics 1013–1017 (Aug. 1983).
Chemical Abstracts, vol. 102, No. 13, Apr. 1, 1985, p. 681 abstract No. 113169e, Columbus, Ohio, U.S.
JP-A-59 167 576 (Kyowa Hakko Kogyo Co., Ltd.) 09-21-1984.
European Search Report-EP 86 10 3996.

*Primary Examiner*—Nicholas S. Rizzo
*Attorney, Agent, or Firm*—Oliff & Berridge

[57] ABSTRACT

The present invention relates to novel cephalosporin derivatives, processes for preparing thereof, compositions for preventing and/or treating infectious diseases which comprise the novel cephalosporin derivatives as active components, and the intermediate compounds in the synthesis of cephalosporin derivatives and processes for producing thereof.

The present invention is based on the selection of groups containing a condensed heterocyclic ring, particularly a triazolopyrimidine ring or a thiadiazolopyrimidine ring, as substituents at the 3-position of the cephem skeleton, and of groups containing a catechol moiety, particularly a catechol carboxymethyloxyimino moiety or a catechol carboxyimino moiety, as substituents at the 7-position of the cephem skeleton.

The compounds of the present invention containing the aforementioned substituents have a strong antibacterial activity against Gram-negative bacteria and also against Gram-positive bacteria including methicillin-resistant *Staphylococcus aureus.* These compounds are extremely useful for the treatment of infectious diseases.

12 Claims, No Drawings

CEPHALOSPORIN DERIVATIVES

BACKGROUND OF THE INVENTION

The present invention relates to novel cephalosporin derivatives, processes for producing cephalosporin derivatives, and compositions containing cephalosporin derivatives for treating and/or preventing infectious diseases.

Developments of cephalosporin derivatives have been remarkable. Some cephalosporin derivatives have been developed which have excellent antibacterial activity against Gram-negative bacteria. However, the antibacterial activity of these cephalosporin derivatives against Gram-positive bacteria is rather poor. Several cephalosporin antibiotics have been used for the treatment of Gram-positive bacteria infections and the increase of Gram-positive bacteria resistant to cephalosporin antibiotics, for example, methicillin-resistant *Staphylococcus aureus* (MRSA), has become widely known year by year.

From the foregoing background, it has been desired to develop cephalosporin derivatives having a strong antibacterial activity against Gram-positive bacteria while retaining a sufficient antibacterial activity against Gram-negative bacteria.

SUMMARY OF THE INVENTION

An object of the present invention is to provide novel cephalosporin derivatives and salts, hydrates and salts of hydrates thereof.

Another object of the present invention is to provide processes for producing novel cephalosporin derivatives.

A further object of the present invention is to provide compositions for preventing and/or treating infectious diseases which comprise novel cephalosporin derivatives as active components.

A further object of the present invention is to provide intermediate compounds in the synthesis of cephalosporin derivatives and processes for producing such intermediate compounds.

The present invention is based on the selection of groups containing a condensed heterocyclic ring, particularly a triazolopyrimidine ring or a thiadiazolopyrimidine ring, as substituents at the 3-position of the cephem skeleton, and of groups containing a catechol moiety, particularly a catechol carboxymethyloxyimino moiety or a catechol carboxyimino moiety, as substituents at the 7-position of the cephem skeleton.

The compounds of the present invention containing these substituents have a wide antibacterial spectrum against Gram-negative bacteria and Gram-positive bacteria including methicillin-resistant *Staphylococcus aureus*. These compounds are extremely useful for the treatment of infectious diseases.

DETAILED DESCRIPTION OF THE INVENTION

As a result of extensive investigations concerning development of cephalosporin derivatives having a satisfactory antibacterial activity against Gram-negative bacteria and also having strong antibacterial activity against Gram positive bacteria, the present inventors have found that cephalosporin derivatives represented by the general formula (I) satisfy these requirements and, have accomplished the present invention.

The present invention is based on the selection of groups containing a condensed heterocyclic ring, particularly a triazolopyrimidine ring or a thiadiazolopyrimidine ring, as substituents at the 3-position of the cephem skeleton, and of groups containing a catechol moiety, particularly a catechol carboxymethyloxyimino moiety or a catechol carboxyimino moiety, as substituents at the 7-position of the cephem skeleton. The present invention is directed to cephalosporin derivatives represented by the general formula (I):

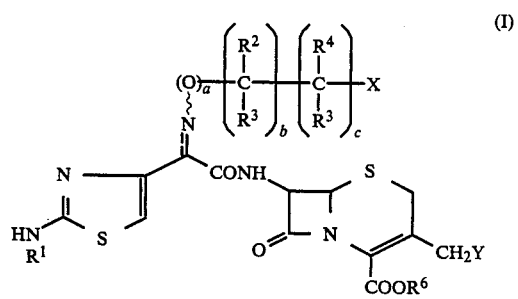

and salts, hydrates and salts of hydrates thereof; wherein $R^1$ represents a hydrogen atom or an amino-protecting group, $R^2$ and $R1$ are the same or different and represent hydrogen atoms, methyl groups, carboxyl groups, protected carboxyl groups, or together an oxygen atom, $R^4$ and $R^5$ represent hydrogen atoms or together an oxygen atom, $R^6$ represents a hydrogen atom or a carboxyl-protecting group, a, b, and c each represents an integer of 0 or 1, the bond shown with a wavy line represents a bond of anti-form or syn-form, the bond shown with a straight line and a dotted line represents a double bond or a single bond, X represents a hydrogen atom, a hydroxyl group or a group:

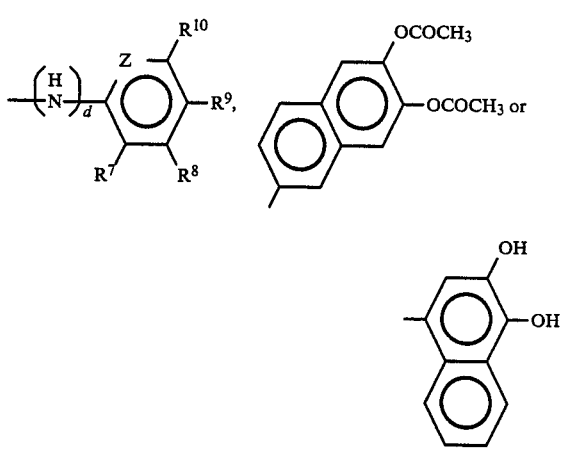

wherein $R^7$ represents a hydrogen atom, a chlorine atom, a carboxyl group, a methyl group, an isopropyl group, a hydroxy group, a methoxy group, or an acetoxy group, $R^8$ and $R^9$ are the same or different and represent hydrogen atoms, chlorine atoms, methyl groups, hydroxy groups, methoxy groups, ethoxy groups, acetoxy groups, chloroacetoxy groups, butanoyloxy groups, methanesulfonyloxy groups, p-toluenesulfonyloxy groups, amino groups, acetamino groups, benzyloxycarbonylamino groups, nitro groups, methanesulfonyl groups, together an ethylenedioxy group, or together a carbonyldioxy group, $R^{10}$ represents a hydrogen atom, a hydroxy group, an acetoxy group, a methyl group, a methoxy group, a nitro group, or a chloroacetoxy group, Z represents a carbon atom or a nitrogen atom, d represents an integer of 0 or 1, and Y represents a halogen atom, an acetoxy group or a group:

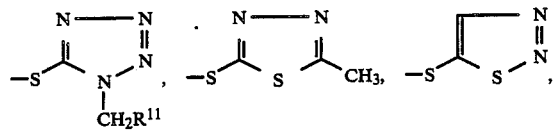

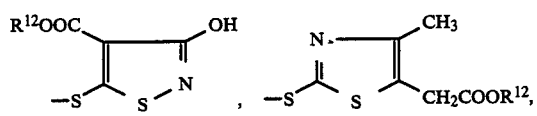

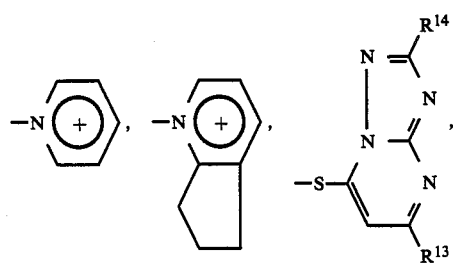

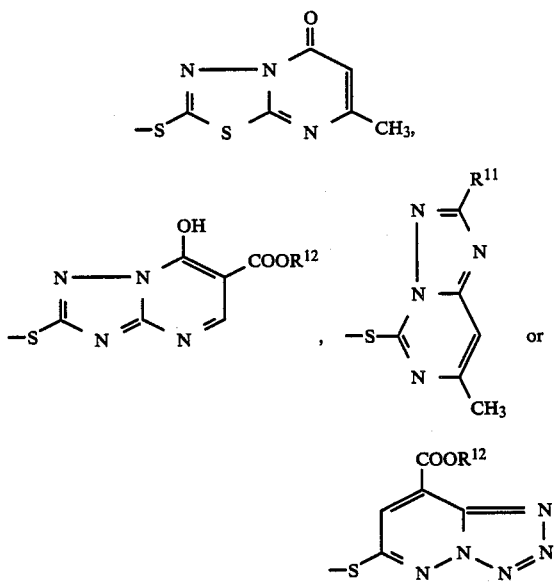

wherein $R^{11}$ represents a hydrogen atom, a carboxyl group, or a protected carboxyl group, $R^{12}$ represents a hydrogen atom or a carboxyl-protecting group, $R^{13}$ represents a methyl group, a hydroxy group, a carboxyl group, a carboxymethyl group, a protected carboxyl group, or a protected carboxymethyl group, and $R^{14}$ represents a hydrogen atom, a carboxyl group, a hydroxysulfonyl group, a protected carboxyl group, or a protected hydroxysulfonyl group.

The present invention is also directed to a process for preparing above-mentioned cephalosporin derivatives. The present invention is further directed to pharmaceutical compositions for treating and/or preventing infectious diseases characterized by containing these cephalosporin derivatives as active components.

In the cephalosporin derivatives of the present invention represented by the general formula (I), it is known that the aminothiazole moiety as the substituent at the 7-position thereof exhibits tautomerism as shown below:

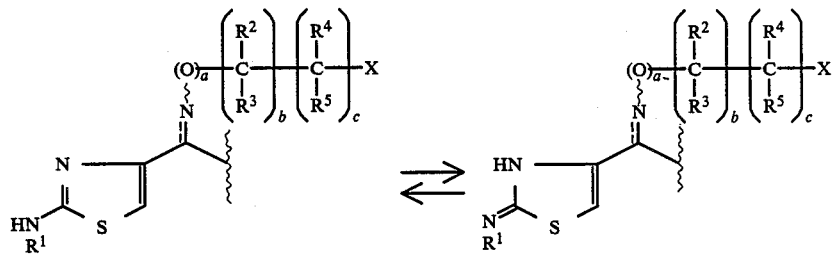

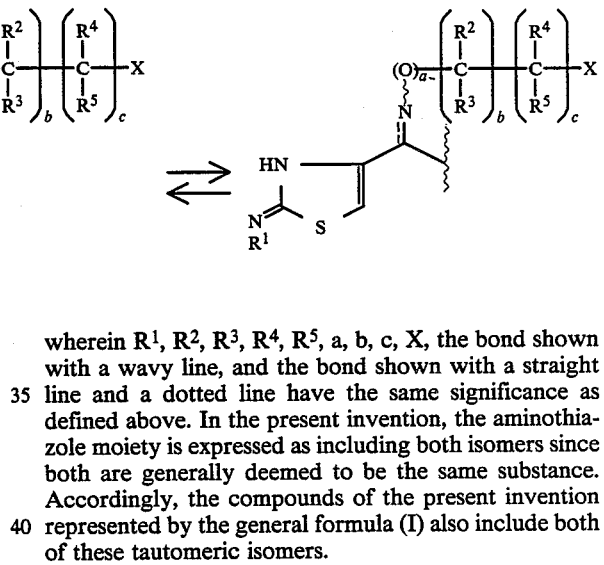

wherein $R^1$, $R^2$, $R^3$, $R^4$, $R^5$, a, b, c, X, the bond shown with a wavy line, and the bond shown with a straight line and a dotted line have the same significance as defined above. In the present invention, the aminothiazole moiety is expressed as including both isomers since both are generally deemed to be the same substance. Accordingly, the compounds of the present invention represented by the general formula (I) also include both of these tautomeric isomers.

The compounds represented by the general formula (I) may form acid or base addition salts. Typical examples of base addition salts of the compounds represented by the general formula (I) include pharmacologically acceptable salts such as alkali metal salts such as sodium salts, potassium salts, etc.; alkaline earth metal salts such as calcium salts, etc.; salts of organic bases such as ammonium salts, benzylamine salts, diethylamine salts, etc.; salts of amino acids such as arginine salts, lysine salts, etc. These salts of the compounds may be a mono-salts, di-salts or tri-salts. In the case of mono-salts or di-salts, the salts may be salts of the carboxyl group at the 2-position and/or salts of the carboxyl or sulfoxy group contained in the substituents at the 3-position, and/or salts of the carboxyl group in the acyl group at the 7-position, of the cephem skeleton.

Typical examples of acid addition salts of the compounds represented by the general formula (I) include pharmacologically acceptable salts, such as salts of inorganic acids such as hydrochlorides, hydrobromides, sulfates, phosphates, etc.; salts of organic acids such as acetates, citrates, maleates, tartarates, benzoates, ascorbates, ethanesulfonates, toluenesulfonates, etc.; salts of amino acids such as aspartates, glutamates, etc. The compounds of the present invention represented by the general formula (I) may be present as a syn-isomer shown below:

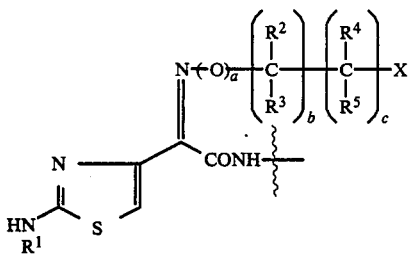

wherein $R^1$, $R^2$, $R^3$, $R^4$, $R^5$, a, b, c, X and the bond shown with a wavy line have the same significance as defined above; or as an anti-isomer shown below:

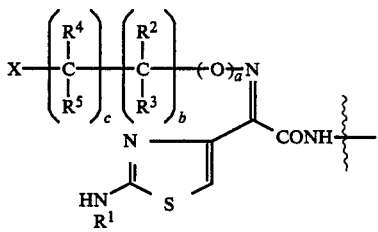

wherein $R^1$, $R^2$, $R^3$, $R^4$, $R^5$, a, b, c, X and the bond shown with a wavy line have the same significance as defined above; or as a mixture of these isomers. Among them, the syn-isomer is particularly preferred and, mixtures mainly composed of the syn-isomer are also preferred.

In the compounds of the present invention represented by the general formula (I), the amino-protecting groups may be selected from acyl groups such as formyl, acetyl, chloroacetyl, t-butoxycarbonyl, benzyloxycarbonyl, etc.; or aralkyl groups such as benzyl, diphenylmethyl, triphenylmethyl, etc. Trimethylsilyl group may also be used as an aminoprotecting group. The carboxyl-protecting groups may be selected from alkyl esters such as methyl ester, ethyl ester, t-butyl ester, etc.; or aralkyl esters such as benzyl ester, diphenylmethyl ester, triphenylmethyl ester, etc.; or trimethylsilyl ester. Inorganic or organic bases may also be used as carboxyl-protecting groups. Collectively taking account of various operations, synthesis of thus protected products, and conditions for the removal of protecting groups, it is preferred to use a triphenylmethyl group as the amino-protecting group and a diphenylmethyl group as the carboxyl-protecting group.

The compounds of the present invention represented by the general formula (I) can be produced as follows. Namely;

Process A

The compounds of the present invention represented by the general formula (I) can be produced by reacting compounds represented by the general formula (II):

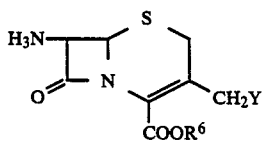

wherein $R^6$ and Y have the same significance as defined above, with compounds represented by the general formula (III):

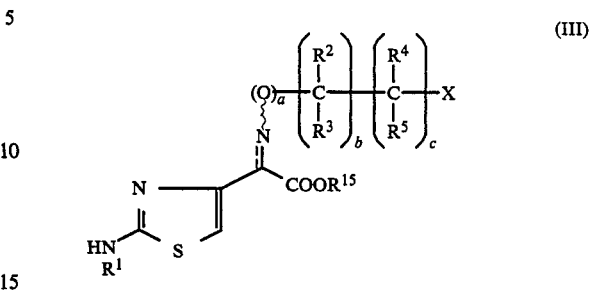

wherein $R^1$, $R^2$, $R^3$, $R^4$, $R^5$, a, b, c, X, the bond shown with a wavy line and the bond shown with a straight line and a dotted line have the same significance as defined above, and $R^{15}$ represents a hydrogen atom or a carboxyl-protecting group.

The compounds represented by the general formula (II) may be reacted with the compounds represented by the general formula (III) using suitable condensing agents, for example, N,N-dicyclohexylcarbodiimide, N-ethyl-5-phenylisoxazolium-3'-sulfonate, etc. Alternatively, the compounds represented by the general formula (III) may be converted into appropriate reactive derivatives prior to the reaction with the compounds represented by the general formula (II). The appropriate reactive derivatives may be, for example, acid halides (e.g., acid chlorides), azides, acid anhydrides, particularly mixed acid anhydride with strong acids, active esters (e.g., N-hydroxysuccinimide ester) or active amides (e.g., imidazolide, triazolide).

The reaction between the compounds represented by the general formula (II) and the compounds represented by the general formula (III) may be carried out generally in an inert organic solvent such as dioxane, tetrahydrofuran, acetonitrile, chloroform, methylene chloride, ethyl acetate, dimethylformamide, etc., if necessary and desired, in the presence of deacidifying agents. The reaction may also be carried out in an aqueous solution, preferably in the presence of deacidifying agents. As the deacidifying agents, triethylamine, diethylaniline, and the like may be used in the organic solvent system, and aqueous alkalis, preferably sodium hydroxide, sodium hydrogen carbonate (sodium bicarbonate), potassium carbonate, and the like may be used in the aqueous system.

The reaction may be carried out at temperatures ranging from about $-30°$ C. to $30°$ C., and preferably from $-10°$ C. to $10°$ C.

If necessary and desired, the protecting groups may be removed from thus obtained cephalosporin derivatives represented by the general formula (I).

The compounds represented by the general formula (II) used in the process of the present invention can be prepared by reacting known 7-amino-cephalosporanic acid with heterocyclic thiols or pyridine derivatives corresponding to group Y, for example, 2-carboxy-7-mercapto-5-methyl-s-triazolo[1,5-a]pyrimidine (Japanese Patent Application No. 247251/1983) or carboxyl-protected derivatives thereof, in a solvent such as alcohols, dimethylformamide, acetonitrile, or water etc. In the case that the reaction is carried out in organic solvents, it is preferred that the reaction be performed in the presence of Lewis acids such as boron trifluoride-ether complexes, etc. Further in the case that water is used as the solvent, the reaction can be carried out in the presence of an appropriate amount of aqueous alkalis such as sodium hydrogen carbonate, potassium carbonate, etc., or using buffers having a pH of 6.0 to 7.8 as the solvent.

The reaction temperature may be in the range of about 40° C. to about 80° C., and preferably from 55° C. to 65° C.

If necessary and desired, the protecting groups may be removed from thus obtained compounds represented by the general formula (II).

PROCESS B

The compounds represented by the general formula (I) can be produced by reacting compounds represented by the general formula (IV):

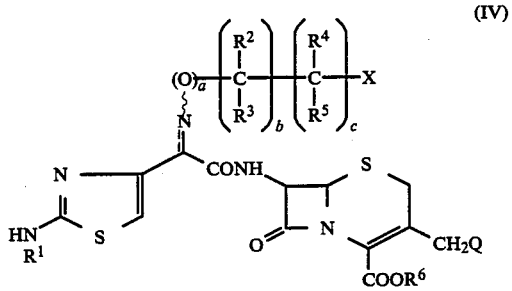

(IV)

wherein $R^1$, $R^2$, $R^3$, $R^4$, $R^5$, a, b, c, X, the bond shown with a wavy line and the bond shown with a straight line and a dotted line have the same significance as defined above, and Q represents a chlorine atom, a bromine atom, an iodine atom, or an acetoxy group, with compounds represented by the general formula (V):

H—Y     (V)

wherein Y has the same significance as defined above.

The reaction between the compounds represented by the general formula (IV) and the compounds represented by the general formula (V) may be carried out in an organic solvent such as alcohols, dimethylformamide, dimethylsulfoxide, dichloromethane, etc. or mixture thereof, or in an aqueous system. Preferably, the reaction of the compounds represented by the general formula (IV) wherein Q represents an acetoxy group, and the compounds represented by the general formula (V) may be carried out in the presence of an appropriate amount of aqueous alkalis, e.g., sodium hydrogen carbonate or potassium carbonate, or carried out in a buffer solution at a pH in the range of 6.0 to 7.8, at temperatures in the range of about 40° C. to about 80° C., and preferably at from 55° to 65° C. Preferably, the reaction of the compounds represented by the general formula (IV) wherein Q represents a halogen atom, and the compounds represented by the general formula (V) may be carried out in an organic solvent at temperatures in the range of about −30° C. to 30° C., and preferably at from −10° C. to 10° C.

If necessary and desired, the protecting groups may be removed from thus obtained cephalosporin derivatives represented by the general formula (I).

The compounds represented by the general formula (IV) wherein Q represents an acetoxy group or a chlorine atom, used in the process of the present invention can be prepared by reacting the compounds represented by the general formula (III) with known 7-amino-cephalosporanic acid or carboxyl-protected derivatives thereof, or with known 3-chloromethyl-7-amino-cephalosporanic acid or carboxyl-protected derivatives thereof by the same manner as described in Process A. the compounds represented by the general formula (IV) wherein Q represents a bromine atom or an iodine atom can be prepared by reacting the compounds represented by the general formula (IV) wherein Q represents a chlorine atom with alkali bromides or iodides such as potassium bromide, potassium iodide, sodium bromide or sodium iodide in an inert organic solvent such as acetone or methylethylketone. If necessary and desired, the reaction may be carried out in the darkness. The reaction temperature may be in the range of about −10° C. to 50° C. and preferably 0° C. to 20° C. If necessary and desired, the protecting groups may be removed from thus obtained cephalosporin derivatives represented by the general formula (IV).

Process C

The compounds represented by the general formula (I) can be produced by reacting compounds represented by the general formula (VI)

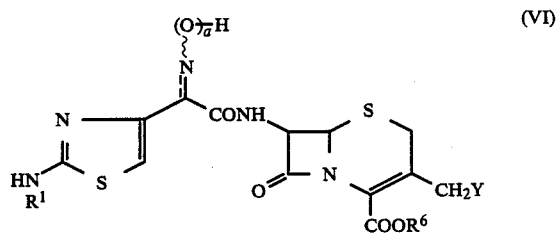

(VI)

wherein $R^1$, $R^6$, Y, a, the bond shown with a wavy line and the bond shown with a straight line and a dotted line have the same significance as defined above, with compounds represented by the general formula (VII)

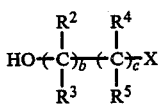

(VII)

wherein $R^2$, $R^3$, $R^4$, $R^5$, b, c and X have the same significance as defined above. The reaction can be carried out by reacting the compounds represented by the general formula (VII) with the compounds represented by the general formula (VI) using a suitable condensing agent such as N,N-dicyclohexylcarbodiimide, triphenylphosphine, diethyl azodicarboxylate, or by reacting the compounds represented by the general formula (VI) with appropriate reactive derivatives of the compounds represented by the general formula (VII); when the compounds represented by the general formula (VII) are acids, they may be converted into acid halides, acid anhydrides or mixed acid anhydrides which are preferably prepared with strong acids, and when the compounds represented by the general formula (VII) are alcohols, they may be converted into alkyl halides or aralkyl tosylates. In view of reactivity, operability, etc., particularly preferred is the process in which the compounds represented by the general formula (VII) are converted into acid halides or aralkyl halides, and reacted with the compounds represented by the general formula (VI).

The reaction between the compounds represented by the general formula (VI) and the compounds represented by the general formula (VII) may be carried out generally in an inert organic solvent such as dioxane, tetrahydrofuran, acetonitrile, chloroform, methylene chloride, acetone, ethyl acetate, or dimethylformamide or in water or in water containing organic solvents, preferably in the presence of deacidifying agents. As the deacidifying agents, triethylamine, diethylamine, etc. may be used in an organic solvent system, and aqueous alkalis, preferably, sodium hydrogen carbonate, sodium carbonate, potassium carbonate, etc. may be used in an aqueous system.

The reaction may be carried out at temperatures ranging from about $-30°$ C. to $30°$ C., and preferably at from $-10°$ C. to $10°$ C.

If necessary and desired, the protecting groups may be removed from thus obtained cephalosporin derivatives represented by the general formula (I).

The compounds represented by the general formula (VII) may be prepared from corresponding precursor by oxidation. For example, 3,4-diacetoxy-2-methyl benzoic acid can be prepared from 3,4-diacetoxy-2-methyl acetophenone by haloform reaction; 3,4-carbonyldioxymandelic acid or 3,4-dihydroxymandelic acid can be prepared from piperonal by conversion into o-chloro-3,4-carbonyldioxyphenylacetic acid, followed by hydroxylation.

PROCESS D

The compounds represented by the general formula (III) can be produced by reacting known compounds represented by the general formula (VIII):

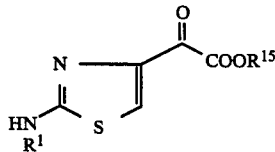

wherein $R^1$ and $R^{15}$ have the same significance as defined above, with compounds represented by the formula (IX):

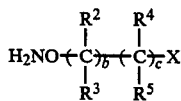

wherein $R^2$, $R^3$, $R^4$, $R^5$, b, c and X have the same significance as defined above.

The reaction between the compounds represented by the general formula (VIII) and the compounds represented by the general formula (IX) may be carried out generally in an inert solvent such as alcohols, dioxane, tetrahydrofuran, acetonitrile, chloroform, methylene chloride, ethyl acetate, dimethylformamide, etc. and, if necessary, using suitable dehydrating agents, e.g., molecular sieves.

The reaction may be carried out at temperatures ranging from about $0°$ C. to $50°$ C., and preferably at from $10°$ C. to $30°$ C.

If necessary and desired, the protecting groups may be removed from thus obtained aminothiazole acetic acid derivatives represented by the general formula (III).

The compounds represented by the general formula (IX) can be prepared by reacting corresponding halides represented by the general formula (X):

wherein $R^2$, $R^3$, $R^4$, $R^5$, b, c and X have the same significance as defined above, and A represents a halogen atom, with N-hydroxyphthalimide, followed by the removal of the phthaloyl group with appropriate deprotecting agents such as N-methylhydrazine, hydrazine hydrate, etc.

The aforementioned halides represented by the general formula (X) can be prepared by halogenation of corresponding precursor. For example, α-bromodiacetoxyphenyl acetic acid can be prepared from diacetoxyphenyl acetic acid by conversion into the acid halide and following bromination with N-bromosuccinimide; α-chloro-3,4-carbonyldioxyphenyl acetic acid can be prepared from piperonal by conversion into 3,4-methylenedioxymandelic acid with bromoform followed by phosphorus pentachloride treatment; 4,5-diacetoxy-2-methylbenzoyl chloride can be prepared from 4,5-diacetoxy-2-methylbenzoic acid with thionyl chloride.

PROCESS E

The compounds represented by the general formula (III) can be produced by reacting compounds represented by the general formula (XI):

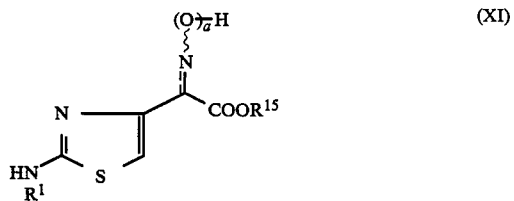

wherein $R^1$, $R^{15}$, a, the bond shown with a wavy line and the bond shown with a straight line and a dotted line have the same significance as defined above, with compounds represented by the general formula (VII):

wherein $R^2$, $R^3$, $R^4$, $R^5$, b, c and X have the same significance as defined above.

The reaction between the compounds represented by the general formula (XI) and the compounds represented by the general formula (VII) may be carried out in the same manner as described in Process C.

If necessary and desired, the protecting groups may be removed from the thus obtained amino thiazole derivatives represented by the general formula (III).

PROCESS F

The compounds represented by the general formula (III) can be produced by reacting compounds represented by the general formula (XII):

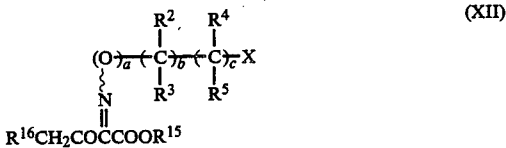

wherein $R^2$, $R^3$, $R^4$, $R^5$, $R^{15}$, a, b, c, X and the bond shown with a wavy line have the same significance as defined above, and $R^{16}$ represents a halogen atom, with compounds represented by the general formula (XIII):

wherein $R^1$ has the same significance as defined above.

The reaction between the compounds. compounds represented by the general formula (XII) and the compounds represented by the general formula (XIII) may be carried out generally in an inert solvent such as methanol, ethanol, isopropanol, dioxane, tetrahydrofuran, acetonitrile, ethyl acetate, or dimethylformamide, etc. If necessary, the reaction may be carried out in the presence of deacidifying agents, such as triethylamine, diethylamine, sodium hydrogen carbonate, sodium carbonate, potassium carbonate, etc.

The reaction may be carried out at temperatures ranging from −10° C. to 10° C. from −10° C. to 10° C.

If necessary and desired, the protecting groups may be removed from thus obtained aminothiazole acetic acid derivatives represented by the general formula (III).

The compounds represented by the general formula (XII) can be prepared by reacting the known compounds represented by the general formula (XIV)

wherein $R^{15}$, $R^{16}$ and the bond shown with a wavy line have the same significance as defined above, with the compounds represented by the general formula (VII)

wherein $R^2$, $R^3$, $R^4$, $R^5$, b, c and X have the same significance as defined above, in the same manner as described in Process C.

To demonstrate the utility of the compounds of the present invention, data on antibacterial activity of representative compounds are shown below.

Compound 1: (6R,7R)-7-[2-(2-amino-4-thiazolyl)-2[Z-(3,4,5-trihydroxybenzoyl)oxyimino]-acetamido]-3-[(2-carboxy-5-methyl-s-triazolo[1,5-a]pyrimidin-7-yl)thiomethyl] 8-oxo-5-thia-1-azabicyclo[4.2.0]oct-2ene-2-carboxylic acid Compound 2: (6R,7R)-7-[2-(2-amino-4-thiazolyl)-2[Z-(4,5-diacetoxy-2-methylbenzoyl)oxyiminoacetamido]-3-[(2-carboxy-5-methyls-triazolo[1,5-a]pyrimidin-7-yl)thiomethyl]-8-oxo-5-thia-1-azabicyclo[4.2.0oct-2-ene-2-carboxylic acid Compound 3: (6R,7R)-7-[2-(2-amino-4-thiazolyl)-2[Z-(4,5-dihydroxy-2-methylbenzoyl)oxy[(2-carboxy-5-methylstriazolo[1,5-a]pyrimidin-7-yl)thiomethyl]-8-oxo-5-thia-1-azabicyclo[4.2.0]oct-2-ene-2-carboxylic acid Compound 4: (6R,7R)-7-[2-(2-amino-4-thiazolyl)-2[Z-(4,5-dihydroxy-2-methylbenzoyl)oxyimino]acetamido-3-[(7-methyl-5H-5-oxo1,3,4-thiadiazolo[3,2-a]pyrimidin-2-yl)thiomethyl]-8-oxo-5-thia-1-azabicyclo[4.2.0]oct-2-ene-2-carboxylic acid Compound 5: (6R,7R)-7-[2-(2-amino-4-thiazolyl)-2[Z-[(4-acetoxy-2-carboxy-5-hydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 6: (6R,7R)-7-[2-(2-amino-4-thiazolyl)-2[Z-[1-(3,4-dihydroxybenzoyl)-1-methyethyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 7: (6R,7R)-7-[2-(2-amino-4-thiazolyl)-2[Z-[(S)-carboxy(3,4-diacetoxyphenyl)methyl]oxyimino]acetamido]-3-[(2-carboxy-5-methyl-s-triazolo[1,5-a]pyrimidin-7-yl)thiomethyl]-8-oxo-5-thia-1azabicyclo[4.2.0]oct-2-ene-2-carboxylic acid Compound 8: (6R,7R)-7-[2-(2-amino-4-thiazolyl)-2[Z-[(R)-carboxy(3,4-diacetoxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 9: (6R,7R)-7-[2-(2-amino-4-thiazolyl)-2[Z-[(S)-carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 10: (6R,7R)-7-[2-(2-amino-4-thiazolyl)-2[Z-[(R)-carboxy(3,4-dihydroxyphenyl)methyl]oxyimino]acetamido]-3-[(2-carboxy-5-methyl-s-triazolo[1,5-a]pyrimidin- 7-yl)thiomethyl]-8-oxo-5-thia-1-azabicyclo[4.2.0]oct-2-ene-2-carboxylic acid Compound 11: (6R,7R)-7-[2-(2-amino-4-thiazolyl)-2[Z-[1-carboxy-1-(3,4-dihydroxyphenyl)ethyl]oxyimino]acetamido]-3-[(2-carboxy-5-methyl-s-triazolo[1,5-a]pyrimidin-7-yl)thiomethyl]-8-oxo-5-thia-1azabicyclo[4.2.0]oct-2-ene-2-carboxylic acid Compound 12: (6R,7R)-7-[2-(2-amino-4-thiazolyl)-2[Z-[carboxy(3,4,5-trihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Compound 13: (6R,7R)-7-[2-(2-amino-4-thiazolyl)-2[Z-[carboxy(3,4-dihydroxyphenyl)methyl]oxyimino]acetamido]-3-[(8-carboxytetrazolo[1,5-b]pyridazin-6-yl)thiomethyl]-8-oxo-5-thia-1-azabicyclo[4.2.0]oct-2-ene-2-carboxylic acid Compound 14: (6R,7R)-7-[2-(2-amino-4-thiazolyl)-2[Z-[carboxy(3,4-dihydroxyphenyl)methyloxyimino]acetamido]- 3-(pyridiniummethyl)-8-oxo-5-thia-1-azabicyclo[4.2.0]oct-2-ene-2-carboxylate Compound 15: (6R,7R)-7-[2-(2-amino-4-thiazolyl)-2[Z-[(S)-carboxy(3,4-dihydroxyphenyl)methyl]ox-yimino]acetamido]-3-(pyridiniummethyl)-8-oxo-5-thia-1-azabicyclo[4.2.0]oct-2-ene-2-carboxylate Compound 16: (6R,7R)-7-[2-(2-amino-4-thiazolyl)-2[Z-[(S)-carboxy(3,4-dihydroxyphenyl)methyl]ox-yimino]acetamido]-3-(2,3cyclopentenopyridinium-methyl)-8-oxo-5-thia-1-azabicyclo-[4.2.0]oct-2-ene-2-carboxylate Compound 17: (6R,7R)-7-[2-(2-amino-4-thiazolyl)-2(3,4-dihydroxybenzoylamino)acetamido]3-[(2-carboxy-5-methyl-s-triazolo[1,5-apyrimidin-7-yl)thiomethyl]-8-oxo-5-thia-1-azabicyclo[4.2.0]oct-2-ene-2-carboxylic acid

EXPERIMENTAL EXAMPLE 1

Antibacterial activity in vitro was determined in accordance with the agar plate dilution method.

A platinum loop each of test bacteria ($10^6$ cells/ml), cultured in Mueller Hinton broth, was inoculated on Mueller Hinton agar plates which contained test compounds at various concentrations. After cultivating at 37° C. for 20 hours, the minimum inhibitory concentration (MIC μg/ml) was determined.

The results are shown in Table 1.

TABLE 1

(MIC μg/ml)

| Compound Number | Staphylococcus aureus Smith | Escherichia coli 67 | Serratia marcescens IFO3759 | Klebsiella pneumoniae IFO3317 | Pseudomonas aeruginosa IFO3445 | Bacteroides fragilis 5524 |
|---|---|---|---|---|---|---|
| 1 | 0.78 | <0.05 | <0.05 | <0.05 | <3.13 | N.D. |
| 2 | 0.78 | <0.05 | <0.05 | <0.05 | 0.20 | N.D. |
| 3 | N.D. | <0.05 | <0.05 | <0.05 | 0.20 | N.D. |
| 4 | 0.39 | 0.78 | <0.05 | <0.05 | 3.13 | N.D. |
| 5 | 1.56 | <0.05 | <0.05 | <0.05 | 0.20 | N.D. |
| 6 | 6.25 | <0.05 | <0.05 | <0.05 | 0.78 | N.D. |
| 7 | N.D. | 0.20 | 0.10 | <0.05 | 1.56 | N.D. |
| 8 | N.D. | 0.20 | 0.10 | <0.05 | 3.13 | N.D. |
| 9 | 0.78 | 0.10 | 0.05 | <0.05 | 1.56 | 6.25 |
| 10 | 0.78 | 0.20 | 0.10 | <0.05 | 6.25 | N.D. |
| 11 | 0.78 | <0.05 | 0.20 | <0.05 | 0.78 | N.D. |
| 12 | 0.78 | 0.10 | N.D. | <0.05 | 6.25 | N.D. |
| 13 | 1.56 | 0.20 | 0.20 | <0.05 | 0.78 | N.D. |
| 14 | 0.78 | 0.39 | 0.39 | 0.10 | 1.56 | N.D. |
| 15 | 0.78 | 0.10 | 0.10 | <0.05 | 0.39 | N.D. |
| 16 | 0.78 | 0.10 | 0.10 | <0.05 | 0.39 | N.D. |
| 17 | 3.13 | <0.05 | <0.05 | <0.05 | 1.56 | N.D. |

N.D.; not determined.

EXPERIMENTAL EXAMPLE 2

Protection ability against systemic infection was determined as follows. An aqueous suspension of test bacteria was intraperitoneally injected into 10 four week old ICR mice. One hour after the infection, test compounds were intravenously administered. The number of surviving mice was counted 1 week after injection to determine the dose at which 50% of the test animals were alive ($ED_{50}$: mg/kg).

The results are shown in Table 2-a through 2-b.

TABLE 2-a

| Compound Number | $ED_{50}$ (mg/Kg) | | | |
|---|---|---|---|---|
| | Escherichia coli 111 | Serratia marcescens 274 | Pseudomonas aeruginosa IFO3445 | Staphylococcus aureus 242* |
| 2 | 2.28 | 3.08 | 212 | 7.90 |
| 3 | N.D. | 1.73 | 407 | 1.79 |
| 5 | N.D. | 2.56 | N.D. | 12.4 |
| 8 | N.D. | 10.5 | N.D. | N.D. |
| 9 | 1.73 | 0.47 | 95.0 | 3.34 |
| 10 | N.D. | 28.6 | N.D. | N.D. |
| 13 | N.D. | 1.05 | N.D. | N.D. |
| CAZ** | 3.91 | 6.41 | 230 | >2100 |
| CMD*** | N.D. | N.D. | N.D. | 8.94 |

N.D.; Not determined.
*; Methicillin-resistant strain
**; Ceftazidime
***; Cefamandole Next, $LD_{50}$ of representative examples of the compounds of the present invention is shown in Table 3 herein $LD_{50}$ was determined in accordance with the Probit method.

TABLE 3

| Compound No. | $LD_{50}$ (mg/Kg, i.v.) |
|---|---|
| 1 | >1000 |
| 2 | >1000 |
| 4 | >1000 |
| 6 | >1000 |
| 9 | >1000 |
| 13 | >1000 |
| 15 | >1000 |
| 16 | >1000 |

The compounds of the present invention are active against microorganisms, such as Gram-positive aerobic bacteria such as *Staphylococcus aureus, streptococci*, etc., Gram-negative aerobic bacteria such as *Escherichia coli, Klebsiella pneumoniae, Proteus mirabilis, Proteus morganii, Serratia marcescens, Pseudomonas aeruginosa, Citrobacter, Enterobacter, Flavobacter*, etc. and anaerobic bacteria such as *Peptococci, Peptostreptococci, Bacteroides*, etc., and are extremely useful for the treatment of infectious diseases such as brain abscess with *Staphylococcus aureus*, bacterial meningitis and purulent meningitis with *Escherichia coli, Hemophilus influenzae*, and *Streptococcus pneumoniae*, infective endocarditis with *Streptococcus epidermidis, Staphylococcus aureus*, and *Klebsiella pneumoniae*, pneumonia with *Pseudomonas* aeruginosa, Hemophilus influenzae, Klebsiella pneumoniae, and Staphylococcus aureus, and pyelonephritis with Escherichia coli, Klebsiella, Proteus and Pseudomonas etc.

The cephalosporin derivatives provided by the present invention can be employed as pharmaceutical compositions, for example, in the form of pharmaceutical compositions containing cephalosporin derivatives together with appropriate, pharmaceutically acceptable carriers. The pharmaceutical composition may take a solid form (for example, tablets, capsules, etc.) or a liquid form (for example, injections, etc.). The compositions may be sterilized and may contain auxiliary agents generally employed in the pharmaceutical art.

Further, it is preferred to use the compounds after they are formed into freeze-dried products or powders followed by dissolving them in a conventional solvent, e.g., water or physiological saline, for use. The compounds can be used orally or parenterally. While dose varies depending upon age and conditions of the patient, conditions and kind of diseases, etc., from about 0.1 to about 10 g, preferably from about 0.2 to about 5 g, can be used as a daily dose for an adult. Parenteral administration of the compounds provided by the present invention is particularly preferred.

Hereafter the present invention will be described with reference to the examples below but is not deemed to be limited thereof.

EXAMPLE 1

Preparation of (6R,7R)-7-[2-(2-amino-4-thiazolyl-)-2-[Z-(3,4,5-trihydroxybenzoyl)oxyimino]acetamido]-3-[(2-carboxy-5-methyl-s-triazolo[1,5-a]-pyrimidin-7-yl)thiomethyl]-8-oxo-5-thia-1-azabicyclo[4.2.0]oct-2-ene-2-carboxylic acid (Compound 1).

Step 1

Preparation of (6R,7R)-7-[2-(2-triphenylmethylamino-4-thiazolyl)-2-[Z-[3,4,5-tris(chloroacetoxy)benzoyl]oxyimino]acetamido]-3-[(2-diphenylmethyloxycarbonyl-5-methyl-s-triazolo[1,5-a]pyrimidin-7-yl)thiomethyl]-8-oxo-5-thia1-azabicyclo[4.2.0]oct-2-ene-2-carboxylic acid diphenylmethyl ester.

To an ice-cooled solution of (6R,7R)-7-[2-(2-triphenylmethylamino-4-thiazolyl)-2-(Z-hydroxyimino)acetamido]3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (0.7 g) in dry dichloromethane (17 ml) was added potassium carbonate (0.1 g) all at once, followed by dropwise addition of a solution of 3,4,5-tris(chloroacetoxy)benzoyl chloride (0.376 g) in dry dichloromethane (10 ml) over a period of five minutes, and the yellow mixture was stirred at 0° C. for 30 minutes. After filtering off the insoluble matters, the filtrate was concentrated under reduced pressure, and the yellow residue was crystallized with ether (50 ml), giving 0.92 g of the objective compound as pale yellow crystals.

Step 2

Preparation of (6R,7R)-7-[2-(2-amino-4-thiazolyl)-2-[Z-[3,4,5-tris(chloroacetoxy)benzoyl]oxyimino]acetamido]-3-[(2-carboxy-5-methyl-s-triazolo[1,5-a]pyrimidin-7-yl)thiomethyl]-8-oxo-5thia-1-azabicyclo[4.2.0]oct-2-ene-2-carboxylic acid.

To a solution of the product obtained in Step 1 (0.9 g) in dichloroethane (7 ml) were added anisole (0.4 ml) and trifluoroacetic acid (0.8 ml) containing a little water under ice cooling, and the resulting yellow solution was stirred at room temperature for two hours. After removing the solvent by decantation, the residue was washed with dichloroethane (10 ml) and crystallized with ether (20 ml) and dichloromethane (30 ml), giving 0.39 g of the objective compound as pale yellow crystals (as trifluoroacetic acid salt).

IR (KBr, cm$^{-1}$): 1781, 1637, 1597, 1509, 1324, 1234, 1170, 1128

NMR (DMSO-d$_6$, δ): 10.1 (1H, d, J=8 Hz), 8.0 (2H, s), 7.4 (1H, s), 7.2 (1H, s), 5.9 (1H, dd, J =5, 8 Hz), 5.3 (1H, d, J =5 Hz), 4.8 (2H, s), 4.7 (4H, s), 4.5 (2H, brs), 3.7 (2H, ABq), 2.6 (3H, s)

Step 3

Preparation of (6R,7R)-7-[2-(2-amino-4-thiazolyl)-2-[Z-(3,4,5-trihydroxybenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 2 (0.3 g) in dimethylacetamide (3 ml) was added thiourea (0.12 g), and the mixture was stirred at room temperature for five hours. The resulting solution was poured into ether (80 ml), and the formed crystals were collected by filtration, and purified by silica gel column chromatography, giving 0.12 g of the objective compound as pale yellow crystals.

IR (KBr, cm$^{-1}$): 1772, 1743, 1685, 1637, 1598, 1509, 1315, 1180

NMR (DMSO-d$_6$, δ): 10.1 (1H, d, J=8 Hz), 7.4 (1H, s), 7.1 (1H, s), 7.0 (2H, s), 6.0 (1H, dd, J=5, 8 Hz), 5.3 (1H, d, 5 Hz), 4.5 (2H, brs), 3.7 (2H, ABq), 2.6 (3H, s)

EXAMPLE 2

Preparation of (6R,7R)-7-[2-(2-amino-4-thiazolyl)-2-[Z-(4,5-diacetoxy-2-methylbenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 2).

Step 1

Preparation of (6R,7R)-7-[2-(2-triphenylmethylamino-4-thiazolyl)-2-[Z-(4,5-diacetoxy-2-methylbenzoyl)oxyimino]acetamido]-3-[(2-diphenylmethyloxycarbonyl-5-methyl-s-triazolo[1,5-a]-pyrimidin-7-yl)thiomethyl]-8-oxo-5-thia-1-azabicyclo[4.2.0]oct-2-ene-2-carboxylic acid diphenylmethyl ester.

To an ice-cooled solution of (6R,7R)-7-[2-(2- triphenylmethylamino-4-thiazolyl)-2-(Z-hydroxyimino)acetamido]-3-[(2-diphenylmethyloxycarbonyl-5-methyl-s-triazolo[1,5-a]pyrimidin-7-yl)thiomethyl]-8-oxo-5 -thia-1-azabicyclo[4.2.0]oct-2-ene-2-carboxylic acid diphenylmethyl ester (0.7 g) in dry dichloromethane (10 ml) was added 4,5-diacetoxy-2-methylbenzoyl chloride (0.19 g) at once and then potassium carbonate (0.083 g). The yellow suspension was stirred at 0° C. for 30 minutes, the insoluble matters were removed by filtration, and the filtrate was washed with brine and dried over anhydrous sodium sulfate. The dried solution was concentrated under reduced pressure, and the residue was crystallized with ether (20 ml), giving 0.80 g of the objective compound as pale yellow crystals.

Step 2

Preparation of (6R,7R)-7-[2-(2-amino-4-thiazolyl)-2-[Z-(4,5-diacetoxy-2-methylbenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 1 (0.70 g) in dichloroethane (7.0 ml) were added anisole (0.35 ml) and trifluoroacetic acid (0.7 ml) under ice cooling, and the resulting yellow solution was stirred at room temperature for two hours. After removing the solvent under reduced pressure, ether (20 ml) was added to the residue to give 0.35 g of the objective compound as milky white crystals (as trifluoroacetic acid salt).

IR (KBr, cm$^{-1}$): 1778, 1637, 1597, 1509, 1206, 1175, 1112

NMR (DMSO-d$_6$, δ): 10.1 (1H, d, J=8 Hz), 7.7 (1H, s), 7.4 (1H, s), 7.3 (1H, s), 7.1 (1H, s), 5.8 (1H, dd, J=6, 8 Hz), 5.3 (1H, d, J=6 Hz), 4.5 (2H, brs), 3.6 (2H, ABq), 2.6 (3H, s), 2.28 (6H, s), 2.24 (3H, s)

EXAMPLE 3

Preparation of (6R,7R)-7-[2-(2-amino-4-thiazolyl)-2-[Z-(4,5-dihydroxy-2-methylbenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 3).

Step 1

Preparation of (6R,7R)-7-[2-(2-triphenylmethylamino-4-thiazolyl)-2-[Z-[4,5-bis(chloroacetoxy)-2-methylbenzoyl]oxyimino]acetamido]-3-[(2-dithyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of (6R,7R)-7-[2-(2-tri phenylmethylamino-4-thiazolyl)-2-(Z-hydroxyimino)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (1.0 g) in dry dichloromethane (24 ml) was added potassium carbonate (0.17 g) at once, followed by dropwise addition of a solution of 4,5-bis(chloroacetoxy)-2-methylbenzoyl chloride (0.43 g) in dry dichloromethane (16 ml) over a period of ten minutes, and the mixture was stirred at 0° C. for three hours. After filtering off the insoluble matters, the filtrate was washed twice with water, once with brine, and dried over anhydrous magnesium sulfate. The dried solution was concentrated under reduced pressure, and the residue was crystallized with ether, giving 1.13 g of the objective compound as pale yellow crystals.

Step 2

Preparation of (6R,7R)-7-[2-(2-amino-4-thiazolyl)-2-[Z-[4,5-bis(chloroacetoxy)-2-methylbenzoyl]oxyimino] acetamido]-3-[(2-carboxy-5-methyl-striazolo[1,5-a]pyrimidin-7-yl)thiomethyl]-8-oxo-5-thia-1-azabicyclo[4.2.0]oct-2-ene-2-carboxylic acid.

To a solution of the product obtained in Step 1 (1.3 g) in dichloroethane (8.3 ml) were added anisole (0.56 ml) and trifluoroacetic acid (1.13 ml) containing a little water under ice cooling, and the resulting yellow solution was stirred at room temperature for three hours. After removing the solvent by decantation, the residue was crystallized with ether, giving 0.57 g of the objective compound as pale yellow crystals (as trifluoroacetic acid salt). IR (KBr, cm$^{-1}$): 1781, 1685, 1597, 1509, 1201, 1182, 1125

NMR (DMSO-d$_6$, δ): 10.1 (1H, d, J=9 Hz), 7.8 (1H, s), 7.4 (2H, s), 7.1 (1H, s), 5.9 (1H, dd, J=5, 9 Hz), 5.2 (1H, d, J=5 Hz), 4.7 (2H, s), 4.6 (2H, s), 4.5 (2H, brs), 3.7 (2H, ABq), 2.6 (3H, s), 2.5 (3H, s)

Step 3

Preparation of (6R,7R)-7-[2-(2-amino-4-thiazolyl)-2-[Z-(4,5-dihydroxy-2-methylbenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 2 (0.56 g) in dimethylacetamide (6 ml) was added thiourea (0.24 g), and the mixture was stirred at room temperature for four hours. The resulting solution was concentrated to about one half of the initial volume under reduced pressure, and the concentrated solution was poured into ether. After removing the solvent by decantation, the residue was treated with dichloromethane, and the formed yellow crystals were purified by silica gel column chromatography, giving 0.37 g of the objective compound as pale yellow crystals.

IR (KBr, cm$^{-1}$): 1778, 1735, 1596, 1509, 1245, 1207, 1129

NMR (DMSO-d$_6$, δ): 10.1 (1H, d, J=7 Hz), 7.4 (1H, s), 7.3 (1H, s), 7.2 (1H, s), 6.7 (1H, s), 6.0 (1H, dd, J=5, 7 Hz), 5.2 (1H, d, J=5 Hz), 4.5 (2H, brs), 3.8 (2H, ABq), 2.6 (3H, s), 2.4 (3H, s)

EXAMPLE 4

Preparation of (6R,7R)-7-[2-(2-amino-4-thiazolyl)-2-[Z-[4,5-bis(chloroacetoxy)-2-methylbenzoyl]oxyimino]acetamido]-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid.

Step 1

Preparation of (6R,7R)-7-amino-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid.

To a suspension of 7-aminocephalosporanic acid (12.24 g) and 2-mercapto-7-methyl-5-oxo-5H-1,3,4thiadiazolo[3,2-a]pyrimidine (9 g) in acetonitrile was added boron trifluoride etherate (26 g), and the mixture was stirred at 60° C for three hours and then overnight at room temperature. Water (70 ml) was added to the solution, and the formed crystals were collected by filtration and washed with water, acetone and ether in this order, giving 4.9 g of the objective compound as pale brown crystals.

IR (KBr, cm$^{-1}$): 1801, 1696, 1570, 1561, 1506, 1472, 1467, 1407, 1393

NMR (DMSO-d$_6$, δ): 6.3 (1H, s), 5.1 (1H, d, J=4 Hz), 4.9 (1H, d, J=4 Hz), 4.4 (2H, ABq), 3.7 (2H, Aq), 2.3 (3H, s)

Step 2

Preparation of (6R,7R)-7-amino-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid diphenylmethyl ester.

To a suspension of the product obtained in Step 1 (4.9 g) in acetone (40 ml) was added diphenyldiazomethane (8.2 g), and the mixture was stirred overnight at room temperature. After filtering off the insoluble matters, the filtrate was concentrated under reduced pressure, and the residue was purified by silica gel column chromatography, giving 2.94 g of the objective compound as yellow crystals.

NMR (DMSO-d$_6$, δ): 7.7 - 7.4 (10H, m), 6.9 (1H, s), 6.3 (1H, s), 5.7 (1H, d, J=4 Hz), 5.2 (1H, d, J=4 Hz), 4.3 (2H, ABq), 3.7 (2H, ABq), 2.3 (3H, s)

Step 3

Preparation of (6R,7R)-7-[2-(2-triphenylmethyl amino-4-thiazolyl)-2-[Z-(1-methoxy-1-methylethyl)o xyimino]acetamido]-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid diphenylmethyl ester.

The product obtained in Step 2 (3.25 g) and 2-(2-triphenylmethylamino-4-thiazolyl)-2-[Z-(1-methoxy-1-methylethyl)oxyimino]acetic acid (5.64 g) were dissolved in dichloromethane (93 ml) and tetrahydrofuran (93 ml) under a nitrogen stream, and the solution was cooled to 0° C. Dicyclohexylcarbodiimide (2.32 g) was added to this solution by small portions, and the mixture was stirred overnight at room temperature. After filtering off the insoluble matters, the filtrate was concentrated under reduced pressure. The residue was redissolved in ethyl acetate and the insoluble matters were filtered off. The filtrate was concentrated under reduced pressure, and the residue was purified by silica gel column chromatography, giving 2.5 g of the objective compound as yellow crystals.

NMR (DMSO-d$_6$, δ): 9.5 (1H, d, J=8 Hz), 8.8 (1H, s), 7.7 - 7.2 (25H, m), 6.9 (1H, s), 6.7 (1H, s), 6.3 (1H, s), 5.8 (1H, dd, J=5, 8 Hz), 5.2 (1H, d, 5 Hz), 4.3 (2H, ABq), 3.8 (2H, ABq), 3.1 (3H, s), 2.3 (3H, s), 1.4 (6H, s)

Step 4

Preparation of (6R,7R)-7-[2-(2-triphenylmethylamino-4-thiazolyl)-2-(Z-hydroxyimino)acetamido]3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid diphenylmethyl ester.

To a solution of the (1.5 g) in acetone (12 ml) was added 1N hydrochloric acid (2.6 ml), and the resulting solution was stirred at room temperature for 3.5 hours. Ethyl acetate was added to the solution, and the organic layer was washed with water, 5% sodium bicarbonate solution and brine in that order, and dried over anhydrous sodium sulfate. The dried solution was concentrated under reduced pressure, and the residue was purified by silica gel column chromatography, giving 1.06 g of the objective compound as milky white crystals.

NMR (DMSO-d$_6$, δ): 11.3 (1H, s), 9.5 (1H, d, J=8 Hz), 8.7 (1H, s), 7.6 - 7.2 (25H, m), 7.0 (1H, s), 6.6 (1H, s), 6.2 (1H, s), 5.8 (1H, dd, J=4, 8 Hz), 5.2 (1H, d, J=4 Hz), 4.3 (2H, ABq), 3.7 (2H, ABq), 2.3 (3H, s)

Step 5

Preparation of (6R,7R)-7-[2-(2-triphenylmethylamino-4-thiazolyl)-2-[Z-[4,5-bis(chloroacetoxy)-2-methylbenzoyl]oxyimino]acetamido]-3-[(7-methyl-5-oxo-5H-1,3,4-thiadiazolo[3,2-a]pyrimidin-2-yl)thiomethyl]-8-oxo-5-thia-1-azabicyclo[4.2.0]-oct-2-ene-2-carboxylic acid diphenylmethyl ester.

To an ice-cooled solution of the product obtained in Step 4 (0.6 g) in dry dichloromethane (15 ml) was added potassium carbonate (0.1 g) at once, followed by dropwise addition of a solution of 4,5-bis(chloroacetoxy)-2-methylbenzoyl chloride (0.25 g) in dry dichloromethane (10 ml). The mixture was stirred under ice cooling for one hour and then at room temperature for an additional two hours. After filtering off the insoluble matters, the filtrate was washed with water and with brine, and dried over anhydrous sodium sulfate. The dried solution was concentrated under reduced pressure, and the residue was purified by silica gel column chromatography, giving 0.47 g of the objective compound.

NMR (DMSO-d$_6$, δ): 10.1 (1H, d, J=8 Hz), 9.0 (1H, s), 7.8 - 7.1 (28H, m), 7.0 (1H, s), 6.3 (1H, s), 5.8 (1H, dd, J=4, 8 Hz), 5.2 (1H, d, J=4 Hz), 4.7 (2H, s), 4.5 (2H, s), 4.3 (2H, ABq), 3.6 (2H, ABq), 2.5 (3H, s), 2.3 (3H, s)

Step 6

Preparation of (6R,7R)-7-[2-(2-amino-4-thiazolyl)-2-[Z-[4,5-bis(chloroacetoxy)-2-methylbenzoyl]oxyimino]acetamido]-3-[(7-methyl-5-oxo-5H-1,3,4-thiadiazolo[3,2-a]pyrimidin-2-yl)thiomethcarboxylic acid.

To a solution of the product obtained in Step 5 (0.47 g) in dichloroethane (3.5 ml) were added anisole (0.23 ml) and trifluoroacetic acid (0.47 ml) under ice cooling, and the resulting solution was stirred at room temperature for five hours. After removing the solvent under reduced pressure, the residue was crystallized with ether, giving 0.3 g of the objective compound (as trifluoroacetic acid salt).

NMR (DMSO-d$_6$, δ):
10.1 (1H, d, J=8 Hz), 7.8 (1H, s), 7.4 (1H, s), 7.2 (1H, s), 6.3 (1H, s), 5.9 (1H, dd, J=4, 8 Hz), 5.2 (1H, d, J=4 Hz), 4.7 (2H, s), 4.6 (2H, s), 4.4 (2H, brs), 3.7 (2H, ABq), 2.5 (3H, s), 2.3 (3H, s)

EXAMPLE 5

Preparation of (6R,7R)-7-[2-(2-amino-4-thiazolyl)-2-[Z-(4,5-dihydroxy-2-methylbenzoyl)oxyimino]acetamido]-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid (Compound 4).

To a solution of the product obtained in Example (0.2 g) in dimethylformamide (3 ml) was added thiourea (0.13 g), and the mixture was stirred at room temperature for 7 hours. Ether was added to the solution, and the formed crystals were washed with dichloromethane, and purified by silica gel column chromatography, giving 0.7 g of the objective compound as milky white crystals.

IR (KBr, cm$^{-1}$): 1773, 1685, 1677, 1648, 1637, 1507, 1474

NMR (DMSO-d$_6$, δ): 10.1 (1H, d, J=8 Hz), 7.3 (1H, s), 7.1 (1H, s), 6.7 (1H, s), 6.3 (1H, s), 5.9 (1H, dd, J= 4, 8 Hz), 5.2 (1H, d, J=4 Hz), 4.4 (2H, brs), 3.6 (2H, ABq), 2.4 (3H, s), 2.3 (3H, s)

EXAMPLE 6

Preparation of (6R,7R)-7-[2-(2-amino-4-thiazolyl)-2-[Z-[(4-acetoxy-2-carboxy-5-hydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 5).

Step 1

Preparation of 2-bromomethyl-4,5-diacetoxybenzoic acid diphenylmethyl ester.

To a suspension of 4,5-diacetoxy-2-methylbenzoic acid (11.9 g) in benzene (140 ml) were added thionyl chloride (14.3 ml) and dimethylformamide (2 drops), and the mixture was stirred at 50° C.–70° C. for one hour. The solvent was removed under reduced pressure, and the residue was redissolved in benzene and concentrated under reduced pressure to remove remaining thionyl chloride. The residue was refluxed with benzene (240 ml), N-bromosuccinimide (8.45 g) and benzoylperoxide (230 mg) for two hours. Refluxing was continued for another two hours after addition of N-bromosuccinimide (8.45 g) and benzoylperoxide (230 mg). The resulting solution was allowed to stand until it reached room temperature, and concentrated under reduced pressure. The residue was dissolved in carbon tetrachloride and the insoluble matters were filtered off, and the filtrate was concentrated under reduced pressure. To a solution of the residue in dichloromethane (250 ml) were added diphenylmethanol (8.7 g) and pyridine (3.82 ml) under ice cooling, and the solution was stirred overnight at room temperature. The resulting solution was washed with 1 N hydrochloric acid and with brine, and dried over anhydrous sodium sulfate. The dried solution was concentrated under reduced pressure, and the residue was purified by silica gel column chromatography, giving 8.8 g of the objective compound.

NMR (CDCl$_3$, δ): 7.9 - 7.2 (12H, m), 7.1 (1H, s), 5.0 (2H, s), 2.3 (6H, s)

Step 2

Preparation of 5-acetoxy-4-hydroxy-2N-phthaloyloxmethylbenzoic acid diphenylmethyl ester.

To a suspension of N-hydroxyphthalimide (2.9 g) in acetonitrile (100 ml) was added triethylamine (2.46 ml) under ice cooling. Then the product obtained in Step 1 (8.8 g) dissolved in acetonitrile (65 ml) was added dropwise, and the mixture was stirred for 15 minutes under ice cooling. N-hydroxyphthalimide (2.9 g) was added and stirring was continued for an additional 10 minutes. Resulting solution was poured into 1N citric acid solution under ice cooling, and extracted twice with ethyl acetate. The organic layer was washed with saturated sodium bicarbonate solution, water and brine in that order, and dried over anhydrous sodium sulfate. The dried solution was concentrated under reduced pressure, and the residue was purified by silica gel column chromatography, giving 3.03 g of the objective compound.

NMR (CDCl$_3$, δ): 7.9 - 7.2 (16H, m), 7.0 (1H, s), 5.6 (2H, s), 2.3 (3H, s)

Step 3

Preparation of 2-(2-triphenylmethylamino-4-thiazolyl)-2-[Z-[(4-acetoxy-5-hydroxy-2-diphenylmethyloxycarbonylphenyl)methyl]oxyimino]acetic acid.

To a solution of the product obtained in Step 2 (1.5 g) in dichloromethane (30 ml) was added methylhydrazine (0.15 ml) slowly under cooling at −60° C. The solution was stirred at −60° C. for ten minutes and at 0° C. for additional four hours. After filtering off the insoluble matters, the filtrate was concentrated under reduced pressure and the residue was dissolved in methanol. This solution was added to a solution of (2-triphenylmethylamino-4-thiazolyl)glyoxylic acid (0.7 g) in methanol (40 ml), and the mixture was stirred at room temperature for one hour. The resulting solution was concentrated under reduced pressure, and the residue was purified by silica gel column chromatography, giving 0.65 g of the objective compound as pale yellow crystals.

NMR (DMSO-d$_6$, δ): 8.8 (1H, brs), 7.8 - 7.0 (28H, m), 6.8 (1H, s), 5.4 (2H, s), 2.3 (3H, s)

Step 4

Preparation of (6R,7R)-7-[2-(2-triphenylmethylamino-4-thiazolyl)-2-[Z-[(4-acetoxy-2-diphenylmethyloxycarbonyl-5-hydroxyphenyl)methyl]oxyimino]acetamido]-3-[(2-diphenylmethyloxycarbonyl-5-methyl-s-triazolo-[1,5-a]pyrimidin-7-yl)thiomethyl]-8-oxo-5-thia-1-azabicyclo[4.2.0]-oct-2-ene-2-carboxylic acid diphenylmethyl ester.

To an ice-cooled solution of the product obtained in Step 3 (0.63 g) and (6R,7R)-7-amino-3-[(2-diphenylmethyloxycarbonyl-5-methyl-s-triazolo[1,5-a]-pyrimidin-7-yl)thiomethyl]-8-oxo-5-thia-1-azabicyclo[-4.2.0]oct-2-ene-2-carboxylic acid diphenylmethyl ester (0.5 g) in dry dichloromethane (20 ml) was added dicyclohexylcarbodiimide (0.178 g), and the mixture was stirred overnight at room temperature. After filtering off the insoluble matters, the filtrate was concentrated under reduced pressure, and the residue was purified by silica gel column chromatography, giving 0.15 g of the objective compound.

NMR (DMSO-d$_6$, δ): 10.5 (1H, s), 9.6 (1H, d), 8.8 (1H, brs), 7.8 (1H, s), 7.7 - 6.9 (50H, m), 6.8 (1H, s), 5.9 (1H, dd), 5.4 (2H, s), 5.3 (1H, d), 4.3 (2H, brs), 3.7 (2H, ABq), 2.6 (3H, s), 2.3 (3H, s)

Step 5

Preparation of (6R,7R)-7-[2-(2-amino-4-thiazolyl)-2-[Z-[(4-acetoxy-2-carboxy-5-hydroxyphenyl)methyl]oxyimino]acetamido]-3-[(2-carboxy-5-methyl-s-triazolo-[1,5-a]pyrimidin-7-yl)thiomethyl]-8-oxo-5-thia-1-azabicyclo[4.2.0]oct-2-ene-2-carboxylic acid.

To an ice-cooled solution of the product obtained in Step 4 (0.3 g) in dichloroethane (5.5 ml) were added anisole (0.2 ml) and trifluoroacetic acid (0.7 ml), and the mixture was stirred at room temperature for two hours. After removing the solvent by decantation, the residue was washed with dichloroethane, and crystallized with ether, giving 0.105 g of the objective compound as pale yellow crystals (as trifluoroacetic acid salt).

IR (KBr, cm$^{-1}$): 1772, 1676, 1637, 1598, 1511, 1202

NMR (DMSO-d$_6$, δ): 9.7 (1H, d, J=8 Hz), 7.6 (1H, s), 7.4 (1H, s), 7.0 (1H, s), 6.8 (1H, s), 5.9 (1H, dd, J=5, 8 Hz), 5.5 (2H, s), 5.2 (1H, d, J=5 Hz), 4.4 (2H, brs), 3.6 (2H, ABq), 2.6 (3H, s), 2.2 (3H, s)

EXAMPLE 7

Preparation of (6R,7R)-7-[2-(2-amino-4-thiazolyl)-2-[Z-[1-(3,4-dihydroxybenzoyl)-1methylethyl]oxyimino]acetamido]-3-[(2-carboxy-5-methyl-s-triazolo-[1,5-a]pyrimidin-7-yl)thiomethyl]-8-oxo-5-thia-1-azabicyclo[4.2.0]oct-2-ene-2carboxylic acid (Compound 6).

Step 1

Preparation of (6R,7R)-7-[2-(2-triphenylmethylamino-4-thiazolyl)-2-[Z-[1-(3,4-diacetoxybenzoyl)-1-methylethyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a solution of 2-(2-triphenylmethylamino-4-thiazolyl)-2-[Z-[1-(3,4-diacetoxybenzoyl)-1-methylethyl]oxyimino]acetic acid (5.1 g) in dry dichloromethane (50 ml) were added (6R,7R)-7-amino-3-[(2-diphenylmethyloxycarbonyl-5-methyl-s-triazolo-[1,5-a]pyrimidin-7-yl)thiomethyl]-8-oxo-5-thia-1-azabicyclo[4.2.0]oct-2-ene-2-carboxylic acid diphenylmethyl ester (5.0 g) and tetrahydrofuran (50 ml). To the mixture was added dicyclohexylcarbodiimide (1.5 g) under ice cooling, and stirring was continued at room temperature for three hours. After filtering off the insoluble matters, the filtrate was concentrated under reduced pressure and ethyl acetate was added to the residue. The insoluble matters were filtered off, and the filtrate was concentrated under reduced pressure. The residue was purified by silica gel column chromatography, giving 3.85 g of the objective compound.

IR (KBr, cm$^{-1}$): 781, 1735, 1686, 1596, 1508, 1372, 1242, 701

NMR (DMSO-d$_6$, δ): 9.7 (1H, d, J=9 Hz), 8.9 (1H, s), 8.3–7.2 (40H, m), 6.9 (1H, s), 6.7 (1H, s), 5.9 (1H, dd, J=5, 9 Hz), 5.3 (1H, d, J=5 Hz), 4.4 (2H, brs), 3.7 (2H, ABq), 2.6 (3H, s), 2.3 (6H, s), 1.5 (6H, s)

Step 2

Preparation of (6R,7R)-7-[2-(2-amino-4-thiazolyl)-2-[Z-[1-(3,4-diacetoxybenzoyl)-1methylethyl]oxyimino]acetamido]-3-[(2-carboxy-5-methyl-s-triazolo-[1,5-a]pyrimidin-7-yl)thiomethyl]-8-oxo-5-thia-1-azabicyclo[4.2.0]oct-2-ene-2-carboxylic acid.

To an ice-cooled solution of the product obtained Step 1 (3.8 g) in dichloroethane (28 ml) were added anisole (1.95 ml) and trifluoroacetic acid (3.8 ml), and the mixture was stirred at room temperature for 3.5 hours. After removing the solvent by decantation, the residue was washed twice with dichloroethane, and crystallized with ether, giving 1.8 g of the objective compound (as trifluoroacetic acid salt).

IR (KBr, cm$^{-1}$): 1774, 1685, 1636, 1598, 1509, 1373, 1203, 1112

NMR (DMSO-d$_6$, δ): 9.7 (1H, d, J=9 Hz), 8.1 - 7.3 (4H, m), 6.7 (1H, s), 5.9 (1H, dd, J=5, 9 Hz), 5.2 (1H, d, J=5 Hz), 4.4 (2H, brs), 3.7 (2H, ABq), 2.6 (3H, s), 2.3 (6H, s), 1.5 (6H, s)

Step 3

Preparation of (6R,7R)-7-[2-(2-amino-4-thiazolyl)-2-[Z-[1-(3,4-dihydroxybenzoyl)-1methylethyl]oxyimino]acetamido]-3-[(2-carboxy-5-methyl-s-triazolo-[1,5-a]pyrimidin-7-yl)thiomethyl]-8-oxo-5-thia-1-azabicyclo[4.2.0]oct-2-ene-2-carboxylic acid.

The product obtained in Step 2 (0.6 g) was suspended in water (20 ml), and the pH of the suspension was adjusted to 8.0 with sodium bicarbonate. After stirring at 30° C. for five hours, the resulting solution was applied to a column of Diaion HP 10. The objective fractions eluted with methanol/water were collected and lyophilized, giving 0.34 g of the objective compound (as sodium salt).

IR (KBr, cm$^{-1}$): 1772, 1598, 1513, 1406, 1363, 1189, 1163

NMR (DMSO-d$_6$, δ): 9.6 (1H, d, J=9 Hz), 7.7 - 6.6 (4H, m), 6.6 (1H, s), 5.8 (1H, dd, J=5, 9 Hz), 5.1 (1H, d, J=5 Hz), 4.6 (2H, ABq), 3.7 (2H, ABq), 2.6 (3H, s), 1.5 (6H, s)

EXAMPLE 8

Preparation of (6R,7R)-7-[2-(2-amino-4-thiazolyl)-2-[Z-[(S)-carbooxy(3,4-diacetoxyphenyl)methyl]oxyimino]acetamido]-3-[(2-carboxy-5-methyl-s-triazolo-[1,5-a]pyrimidin-7-yl)thiomethyl]-8-oxo-5-thia-1-azabicyclo[4.2.0]oct-2-ene-2-carboxylic acid (Compound 7).

Step 1

Preparation of 2-bromo-(3,4-diacetoxyphenyl)acetic acid.

Thionyl chloride (60 ml) was added to a suspension of 3,4-diacetoxyphenylacetic acid (51.1 g) in carbon tetrachloride (105 ml) and the mixture was heated at 70° C. for one hour. After cooling to room temperature, N-bromosuccinimide (42.3 g), carbon tetrachloride (105 ml) and a little amount of hydrobromic acid were added, and the mixture was heated for an additional one hour. The resulting mixture was concentrated under reduced pressure, and the residue was redissolved in carbon tetrachloride. After filtering off the insoluble matters, the filtrate was dissolved in acetone (400 ml) and the pH of the solution was adjusted to 4.0 with saturated sodium bicarbonate aqueous solution under ice cooling. The resulting mixture was extracted with chloroform. The chloroform layer was washed with brine and dried over anhydrous sodium sulfate. The dried solution was concentrated under reduced pressure, giving 61.4 g of the objective compound.

NMR (CDCl$_3$, δ) 9.0 (1H, brs), 7.5–7.1 (3H, m), 5.3 (1H, s), 2.3 (6H, s)

Step 2

Preparation of 2-bromo-(3,4-diacetoxyphenyl)acetic acid diphenylmethyl ester.

To a solution of the product obtained in Step 1 (61.4 g) in acetone (500 ml) was added diphenyldiazomethane, and the solution was stirred at room temperature for one hour. The resulting solution was concentrated under reduced pressure and the residue was purified by silica gel column chromatography, giving 48.4 g of the objective compound.

IR (KBr, cm$^{-1}$): 1772, 1756, 1752, 1505, 1371, 1259, 1212, 1113,

NMR (CDCl$_3$, δ):
7.4–7.1 (13H, m), 6.9 (1H, s), 5.4 (1H, s), 2.3 (6H, s)

Step 3

Preparation of 2-N-phthaloyloxy-(3,4-diacetoxyphenyl)acetic acid diphenylmethyl ester.

To an ice-cooled suspension of N-hydroxyphthalimide (15.9 g) in acetonitrile (300 ml) were added triethylamine (13.6 ml) and a solution of the product obtained in Step 2 (48.4 g) in acetonitrile (200 ml). The mixture was stirred under ice cooling for 1.5 hours. The resulting solution was concentrated under reduced pressure and redissolved in ethyl acetate. The solution was washed with water, 1N citric acid solution and with brine in that order. The washed solution was dried over anhydrous sodium sulfate and concentrated under reduced pressure, and the residue was purified by silica gel column chromatography, giving 15.3 g of the objective compound.

IR (KBr, cm$^{-1}$): 1772, 1735, 1506, 1371, 1260, 1209, 1186, 1114, 700

NMR (CDCl$_3$, δ): 7.7 (4H, s), 8.0 - 7.1 (13H, m), 6.9 (1H, s), 2.3 (6H, s)

Step 4

Preparation of 2-aminooxy-(3,4-diacetoxyphenyl)acetic acid diphenylmethyl ester.

To a solution of the product obtained in Step 3 (15.3 g) in dichloromethane (200 ml) was added methylhydrazine (1.34 ml) slowly at −60° C., and the mixture was allowed to stand until room temperature was reached. After stirring for two hours, methylhydrazine (0.07 ml) was added to the mixture, followed by stirring for an additional 30 minutes. The insoluble matters were filtrated off, the filtrate was concentrated under reduced pressure, and the residue was purified by silica gel column chromatography, giving 8.7 g of the objective compound.

IR (KBr, cm$^{-1}$): 1772, 1752, 1506, 1371, 1256, 1210, 1180, 1113, 702

NMR (CDCl$_3$, δ): 7.7-7.0 (13H, m), 6.9 (1H, s), 5.2 (1H, s), 2.27 (3H, s), 2.26 (3H, s)

Step 5

Preparation of 2-(2-triphenylmethylamino-4-thiazolyl)-2-[Z-[diphenylmethyloxycarbonyl(3,4-diacetoxyphenyl)methyl]oxyimino]acetic acid.

To a solution of (2-triphenylmethylamino-4-thiazolyl)glyoxylic acid (7.62 g) in methanol (400 ml) was added dropwise a solution of the product obtained in Step 4 (8.7 g) in methanol (150 ml). The mixture was stirred at room temperature for 1.5 hours, and concentrated under reduced pressure, giving 16.0 g of the objective compound as crude product.

IR (KBr, cm$^{-1}$): 1772, 1256, 1209, 1180, 754, 701

NMR (DMSO-d$_6$, δ): 8.9 (1H, s), 7.8-7.2 (28H, m), 6.9 (1H, s), 6.8 (1H, s), 5.9 (1H, s), 2.3 (6H, s)

Step 6

Preparation of (6R,7R)-7-[2-(2-triphenylmethylamino-4-thiazolyl)-2-[Z-[diphenylmethyloxycarbonyl(3,4-diacetoxyphenyl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of the crude product obtained in Step 5 (5.6 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (5.0 g) in dichloromethane (170 ml) was added dicyclohexylcarbodiimide (1.4 g), and the mixture was stirred at room temperature for five hours. After filtering off the insoluble matters, the filtrate was concentrated under reduced pressure. The residue was dissolved in ethyl acetate and the insoluble matters were filtered off. The filtrate was washed with brine and dried over anhydrous sodium sulfate. The dried solution was concentrated under reduced pressure, and the residue was purified by silica gel column chromatography, giving 0.73 g (less polar form) and 1.39 g (more polar form) of the objective compounds.

less polar form

IR (KBr, cm$^{-1}$): 1780, 1742, 1737, 1507, 1249, 1205, 1182, 700

NMR (DMSO-d$_6$, δ): 9.7 (1H, d, J=8 Hz), 8.9 (1H, brs), 7.5-7.1 (50H, m), 6.9 (1H, s), 6.82 (1H, s), 6.78 (1H, s), 5.9 (1H, s), 5.8 (1H, dd, J=4, 8 Hz), 5.2 (1H, d, J=4 Hz), 4.3 (2H, brs), 3.6 (2H, ABq), 2.6 (3H, s), 2.2 (6H, s)

more polar form

IR (KBr, cm$^{-1}$): 1780, 1742, 1596, 1507, 1450, 1372, 1205, 1182, 700

NMR (DMSO-d$_6$, δ): 9.7 (1H, d, J=9 Hz), 8.9 (1H, s), 7.4-7.2 (50H, m), 7.0 (1H, s), 6.82 (1H, s), 6.76 (1H, s), 5.9 (1H, s), 5.9 (1H, dd, J=4, 9 Hz), 5.2 (1H, d, J=4 Hz), 4.3 (2H, brs), 3.7 (2H, ABq), 2.6 (3H, s), 2.20 (6H, s)

Step 7

Preparation of (6R,7R)-7-[2-(2-amino-4-thiazolyl)-2-[Z-[(S)-carboxy(3,4-diacetoxyphenyl)methyl]oxyimino]acetamido]-3-[(2-carboxy-5-methyl-s-triazolo[1,5-a]pyrimidin-7-yl)thio-8-oxo-5-thia-1-azabicyclo[4.2.0]oct-2-ene-2-carboxylic acid.

To a solution of the less polar form of the product obtained in Step 6 (0.73 g) in dichloroethane (3 ml) were added anisole (0.4 ml) and trifluoroacetic acid (0.8 ml) under ice cooling, and the resulting solution was stirred at room temperature for three hours. Additional trifluoroacetic acid (0.6 ml) was added and the mixture was stirred for another 30 minutes. After removing the solvent by decantation, the residue was washed with dichloroethane and crystallized with ether, giving 0.3 g of the objective compound (as trifluoroacetic acid salt).

IR (KBr, cm$^{-1}$):
1773, 1735, 1684, 1637, 1598, 1509, 1373, 1206, 1186

NMR (DMSO-d$_6$, δ): 9.6 (1H, d, J=8 Hz), 7.6 - 7.2 (4H, m), 6.8 (1H, s), 5.8 (1H, dd, J=4, 8 Hz), 5.6 (1H, s), 5.2 (1H, d, J=4 Hz), 4.4 (2H, brs), 3.72 (1H, d, J=22 Hz), 3.48 (1H, d, 22 Hz), 2.6 (3H, s), 2.2 (6H, s)

[α]$^{25}$ −2.9° (c=1.0, methanol:acetone=1:1)

EXAMPLE 9

Preparation of (6R,7R)-7-[2-(2-amino-4-thiazolyl)-2-[Z-[(S)-carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 9).

The product obtained in Step 7 of Example 8 (0.27 g) was suspended in water (11 ml), and the pH of the mixture was adjusted to 8.0 with sodium bicarbonate. After stirring at room temperature for six hours, the resulting solution was applied to a Diaion HP 10 column. The objective fractions eluted with water were collected and lyophilized, giving 0.14 g of the objective compound (as sodium salt).

IR (KBr, cm$^{-1}$) 1763, 1599, 1514, 1474, 1404, 1360, 1314

NMR (D$_2$O, δ): 7.2 (1H, s), 7.0 - 6.8 (4H, m), 5.7 (1H, d, J=5 Hz), 5.4 (1H, s), 5.0 (1H, d, J=5 Hz), 4.3 (2H, ABq), 3.4 (2H, ABq), 2.6 (3H, s)

[α]$^{25}$ +27.4° (c=1.0, water)

EXAMPLE 10

Preparation of (6R,7R)-7-[2-(2-amino-4-thiazolyl)-2-[Z-[(R)-carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 10).

Step 1

Preparation of (6R,7R)-7-[2-(2-amino-4-thiazolyl)-2-[Z-[(R)-carboxy(3,4-diacetoxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the more polar form of the product obtained in Step 6 of Example 8 (1.3 g) in dichloroethane (6 ml) were added anisole (0.8 ml) and trifluoroacetic acid (1.6 ml) under ice cooling, and the resulting solution was stirred at room temperature for 4 hours. After addition of dichloroethane (6 ml), the solvent was removed by decantation. The residue was washed with dichloroethane, and crystallized with ether, giving 0.78 g of the objective compound (as trifluoroacetic acid salt).

IR (KBr, cm$^{-1}$):
1773, 1735, 1683, 1636, 1598, 1509, 1373, 1205, 1185
NMR (DMSO-d$_6$, δ):
9.7 (1H, d, J=9 Hz), 7.4–7.2 (4H, m), 6.8 (1H, s), 5.8 (1H, dd, J=4, 9 Hz), 5.6 (1H, s), 5.2 (1H, d, J=4 Hz), 4.5 (2H, brs), 3.79 (1H, d, J=17 Hz), 3.60 (1H, d, J=17 Hz), 2.6 (3H, s), 2.3 (6H, s)
[α]$^{25}$ −17.4° (c=1.0, methanol:acetone=1:1)

Step 2

Preparation of (6R,7R)-7-[2-(2-amino-4-thiazolyl)-2-[Z-[(R)-carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The product obtained in Step 1 (0.5 g) was suspended in water (20 ml), and the pH of the mixture was adjusted to 7.6–8.0 with sodium bicarbonate. After stirring at room temperature for six hours, the resulting solution was applied to a Diaion HP 10 column. The objective fractions eluted with water were collected and lyophilized, giving 0.2 g of the objective compound (as sodium salt).

IR (KBr, cm$^{-1}$): 1763, 1601, 1516, 1474, 1404, 1358, 1314
NMR (D$_2$O, δ): 7.2 (1H, s), 7.0 - 6.9 (4H, m), 5.6 (1H, d, J=5Hz), 5.4 (1H, s), 5.0 (1H, d, J=5 Hz), 4.4 (2H, ABq), 3.4 (2H, ABq), 2.6 (3H, s) [α]$^{25}$ +21.8° (c=1.0, water)

EXAMPLE 11

Preparation of (6R,7R)-7-[2-(2-amino-4-thiazolyl)-2-[Z-[carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo5-thia-1-azabicyclo[4.2.0]oct-2-ene-2-carboxylic acid.

Step 1

Preparation of 2-(2-amino-4-thiazolyl)-2-[Z-[diphenylmethyloxycarbonyl(3,4-diacetoxyphenyl) methyl]oxyimino]acetic acid.

To an ice-cooled solution of product obtained in Step 4 of Example 8 (5.3 g) in dimethylformamide (18 ml) was added (2-aminothiazol-4-yl)glyoxylic acid (2.03 g), and the mixture was stirred overnight at room temperature. The resulting solution was poured into ice water (100 ml), and the mixture was acidified (pH 2) with 1 N hydrochloric acid and extracted with ethyl acetate. The organic layer was washed with brine and dried over anhydrous magnesium sulfate. The dried solution was concentrated under reduced pressure, and the residue was crystallized with ether, giving 6.30 g of the objective compound.

NMR (DMSO-d$_6$, δ):
7.5–7.2 (15H, m), 6.85 (1H, s), 6.83 (1H, s), 5.9 (1H, s), 2.3 (6H, s)

Step 2

Preparation of (6R,7R)-7-[2-(2-amino-4-thiazolyl)-2-[Z-[diphenylmethyloxycarbonyl(3,4-diacetoxyphenyl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution containing the product obtained in Step 1 (3.0 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (3.75 g) in dichloromethane (100 ml) was added dicyclohexylcarbodiimide (1.54 g), and the mixture was stirred at room temperature. After filtering off the insoluble matters, the filtrate was concentrated under reduced pressure, and the residue was purified by silica gel column chromatography, giving 4.8 g of the objective compound.

NMR (DMSO-d$_6$, δ): 9.9 and 9.8 (1H, d, J=8 Hz), 7.4–6.8 (38H, m), 5.9 (1H, m), 5.9 (1H, s), 5.3 and 5.2 (1H, d, J=5 Hz), 4.3 (2H, brs), 3.6 (2H, ABq), 2.6 (3H, s), 2.3 (3H, s), 2.2 (3H, s)

Step 3

Preparation of (6R,7R)-7-[2-(2-amino-4-thiazolyl)-2-[Z-[carboxy(3,4-diacetoxyphenyl)methyl]oxyimino]acetamido]-3-[(2-carboxy-5-methyl-striazolo[1,5-a]pyrimidin-7-yl)thiomethyl]-8-oxo-5-thia-1-azabicyclo[4.2.0]oct-2-ene-2-carboxylic acid.

To a solution of the product obtained in Step 2 (0.87 g) in dichloroethane (1.6 ml) were added anisole (0.8 ml) and trifluoroacetic acid (2.4 ml) under ice cooling, and the resulting solution was stirred at room temperature for two hours. After removing the solvent by decantation, the residue was washed with dichloroethane and crystallized with ether, giving 0.6 g of the objective compound (as trifluoroacetic acid salt).

NMR (DMSO-d$_6$, δ): 9.8 and 9.6 (1H, d, J=8 Hz), 7.4–6.9 (4H, m), 6.83 and 6.79 (1H, s), 5.8 (1H, m), 5.6 (1H, s), 5.2 (1H, m), 4.4 (2H, brs), 3.7 (2H, ABq), 2.6 (3H, s), 2.26 (3H, s), 2.24 (3H, s)

Step 4

Preparation of (6R,7R)-7-[2-(2-amino-4-thiazolyl)-2-[Z-[carboxy(3,4-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The product obtained in Step 3 (0.25 g) was suspended in water (10 ml), and the pH of the mixture was adjusted to 8.0 with sodium bicarbonate. After stirring at room temperature for 6 hours, the resulting solution was applied to a Diaion HP 10 column. The objective fractions eluted with water were collected and lyophilized, giving 0.14 g of the objective compound (as sodium salt).

NMR (D$_2$O, δ): 7.2–6.9 (5H, m), 5.7 (1H, m), 5.4 (1H, s), 5.0 (1H, m), 4.3 (2H, ABq), 3.4 (2H, ABq), 2.6 (3H, s)

EXAMPLE 12

Preparation of (6R,7R)-7-[2-(2-amino-4-thiazolyl)-2-[Z-[1-carboxy-1-(3,4-dihydroxyphenyl)ethyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 11).

Step 1

Preparation of α-bromo-α-methyl-3,4-diacetoxyphenylacetic acid diphenylmethyl ester.

To a suspension of o-methyl-3,4,-diacetoxyphenyl acetic acid (10.0 g) in carbon tetrachloride (10 ml) were added thionyl chloride (12 ml) and a little amount of dimethylformamide, and the mixture was stirred at 70° C. for 30 minutes. The solvent was removed under reduced pressure, and the residue was redissolved in carbon tetrachloride (20 ml). Thionyl chloride (5 ml), N-bromosuccinimide (7.22 g) and hydrobromic acid (0.1 ml) were added to the solution, and the mixture was stirred at 85° C. for 1.5 hours. After filtering off the insoluble matters, the filtrate was concentrated under reduced pressure. The residue was dissolved in acetone (60 ml), and the pH of the solution was adjusted to 5 with saturated sodium bicarbonate solution under ice cooling, then to 1 with 1N hydrochloric acid. The acidified mixture was extracted with ethyl acetate (400 ml), and the extract was washed with brine and dried over anhydrous sodium sulfate. The dried solution was concentrated under reduced pressure, and the residue was dissolved in acetone (60 ml) and diphenyldiazomethane (7.0 g) was added. The solution was stirred overnight and the resulting solution was concentrated under reduced pressure. The residue was purified by silica gel column chromatography, giving 4.1 g of the objective compound.

NMR (CDCl$_3$, δ): 7.4–7.0 (13H, m), 6.9 (1H, s), 2.28 (6H, s), 2.27 (3H, s)

Step 2

Preparation of α-methyl-α-phthaloyloxy-3,4-diacetoxyphenylacetic acid diphenylmethyl ester.

To an ice-cooled solution of the product obtained in Step 1 (4.1 g) were added N-hydroxyphthalimide (1.31 g) and then anhydrous potassium carbonate over a period of 10 minutes. After stirring at room temperature for 1.5 hours, the resulting solution was poured into 1 N citric acid aqueous solution (100 ml) and extracted with ethyl acetate (100 ml). The extract was washed thrice with brine and dried over anhydrous sodium sulfate. After concentrating under reduced pressure, the residue was purified by silica gel column chromatography, giving 1.3 g of the objective compound.

IR (KBr, cm$^{-1}$): 1773, 1741, 1736, 1372, 1263, 1208, 1191, 1170, 1119, 702

NMR (CDCl$_3$, δ): 7.8 (4H, m), 7.4–7.2 (13H, m), 6.9 (1H, s), 2.28 (3H, s), 2.27 (3H, s), 1.9 (3H, s)

Step 3

Preparation of α-aminooxy-α-methyl-3.4-diacetoxyphenylacetic acid diphenylmethyl ester.

To a solution of the product obtained in Step 2 (1.3 g) in dry dichloromethane (20 ml) was added methylhydrazine (0.2 g) at −70° C. under a nitrogen stream, and the solution was stirred at −70° C. for 10 minutes and ten at 0° C. for 40 minutes. After filtering off the insoluble matters, the filtrate was concentrated under reduced pressure, and the residue was purified by silica gel column chromatography, giving 0.61 g of the objective compound.

NMR (CDCl$_3$, δ): 7.3–7.0 (13H, m), 6.9 (1H, s), 2.28 (3H, s), 2.26 (3H, s), 1.9 (3H, s)

Step 4

Preparation of 2-(2-triphenylmethylamino-4-thiazolyl)-2-[Z-[1-diphenylmethyloxycarbonyl-1-(3,4-diacetoxyphenyl)ethyl]oxyimino]acetic acid.

To a solution of (2-triphenylmethylamino-4-thiazolyl)glyoxylic acid (0.49 g) in methanol (25 ml) was added dropwise a solution of the product obtained in Step 3 (0.61 g) in methanol (10 ml). The mixture was stirred at room temperature for 1.5 hours and concentrated under reduced pressure. The residue was purified by silica gel column chromatography, giving 0.8 g of the objective compound.

IR (KBr, cm$^{-1}$): 1773, 1751, 1743, 1262, 1209, 1168, 1115, 701

NMR (DMSO-d$_6$, δ): 8.8 (1H, s), 7.3 - 7.1 (28H, m), 6.8 (1H, s), 6.7 (1H, s), 2.3 (6H, s), 1.9 (3H, s)

Step 5

Preparation of (6R,7R)-7-[2-(2-triphenylmethylamino-4-thiazolyl)-2-[Z-[1-diphenylmethyloxycarbonyl-1-(3,4-diacetoxyphenyl)ethyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of the product obtained in Step 4 (0.8 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (0.7 g) in dichloromethane (30 ml) was added dicyclohexylcarbodiimide (0.19 g), and the mixture was stirred overnight at room temperature. After filtering off the insoluble matters, the filtrate was concentrated under reduced pressure, and the residue was purified by silica gel column chromatography, giving 0.6 g of the objective compound.

IR (KBr, cm$^{-1}$): 1791, 1774, 1741, 1736, 1507, 1207, 1171, 700

NMR (DMSO-d$_6$, δ):
9.9 and 9.7 (1H, d, J=8 Hz), 8.9 (1H, s), 7.5–6.8 (53H, m), 5.9 - 5.7 (1H, m), 5.2 (1H, d, J=5 Hz), 4.3 (2H, brs), 3.7 (2H, ABq), 2.6 (3H, s), 2.23 (3H, s), 2.19 (3H, s), 1.9 (3H, s)

Step 6

Preparation of (6R,7R)-7-[2-(2-amino-4-thiazolyl)-2-[Z-[1-carboxy-1-(3,4-diacetoxyphenyl)ethyl]oxyimino]acetamido]-3-[(2-carboxy5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 5 (0.6 g) in dichloroethane (1 ml) were added anisole (0.5 ml) and trifluoroacetic acid (1 ml) under ice cooling, and the mixture was stirred at room temperature for 2 hours. Trifluoroacetic acid (1 ml) was added again and the mixture was stirred overnight at room temperature. After addition of dichloroethane (20 ml) to the resulting solution, the solvent was removed by decantation, and the residue was crystallized with ether, giving 0.31 g of the objective compound (as trifluoroacetic acid salt).

IR (KBr, cm$^{-1}$): 1772, 1735, 1683, 1636, 1597, 1509, 1263, 1232, 1203, 1172

NMR (DMSO-d$_6$, δ): 9.8–9.7 (1H, m), 7.4–7.0 (4H, m), 6.78 and 6.74 (1H, s), 5.8–5.7 (1H, m), 5.3–5.2 (1H, m), 4.4 (2H, brs), 3.7–3.6 (2H, m), 2.6 (3H, s), 2.2 (6H, s), 1.8 (3H, brs)

Step 7

Preparation of (6R,7R)-7-[2-(2-amino-4-thiazolyl)-2-[Z-[1-carboxy-1-(3,4-dihydroxyphenyl)ethyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The product obtained in Step 6 (0.28 g) was suspended in water (11 ml), and the pH of the mixture was adjusted to 8.5 with sodium bicarbonate. The mixture was stirred at room temperature for 5.5 hours, and the resulting solution was applied to a Diaion HP 10 column. The objective fractions were collected and lyophilized, giving 0.094 g of the objective compound (as sodium salt).

IR (KBr, cm$^{-1}$): 1772, 1596, 1509, 1404, 1395, 1389, 1355, 1311

NMR (D$_2$O, δ): 7.2–6.8 (5H, m), 5.8–5.7 (1H, m), 5.2–5.1 (1H, m), 4.5 (2H, ABq), 3.5 (2H, ABq), 2.6 (3H, s), 1.8 (3H, s)

EXAMPLE 13

Preparation of (6R,7R)-7-[2-(2-amino-4-thiazolyl)-2-[Z-[carboxy(3,4,5-trihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 12).

Step 1

Preparation of α-bromo-3,4,5-triacetoxyphenylacetic acid diphenylmethyl ester.

To a suspension of 3,4,5-triacetoxyphenylacetic acid (34.5 g) in carbon tetrachloride (90 ml) were added thionyl chloride (32.5 ml) and dimethylformamide (0.2 ml) and the mixture was stirred at 60° C. for one hour, and cooled to room temperature. Then N-bromosuccinimide (23.7 g), carbon tetrachloride (60 ml) and a little amount of hydrobromic acid were added and the mixture was stirred at 60° C. for three hours. Insoluble matters were filtered off, and the filtrate was concentrated under reduced pressure. The residue was dissolved in acetone (200 ml) and the pH of the solution was adjusted to 5.0 with saturated sodium bicarbonate solution, then to 1 with 1N hydrochloric acid under ice cooling. The acidified mixture was diluted with water, and extracted with ethyl acetate. The extract was washed with brine, dried over anhydrous sodium sulfate, and concentrated under reduced pressure. The residue was dissolved in acetone (200 ml) and diphenyldiazomethane (20.5 g) was added. The solution was stirred at room temperature for one hour. The resulting solution was concentrated under reduced pressure, and the residue was purified by silica gel column chromatography, giving 30 g of the objective compound.

NMR (DMSO-d$_6$, δ): 7.5–7.3 (12H, m), 6.9 (1H, s), 6.2 (1H, s), 2.3 (9H, s)

Step 2

Preparation of o-N-phthaloyloxy-3,4,5-triacetoxyphenylacetic acid diphenylmethyl ester.

To a ice-cooled solution of N-hydroxyphthalimide (8.8 g) in acetonitrile (180 ml) was added triethylamine (7.5 ml), then a solution of the product obtained in Step 1 (30 g) in acetonitrile (120 ml), and the mixture was stirred under ice cooling for 15 minutes. Ethyl acetate (1.5 l) was added, and the resultant solution was washed with an ice-cooled solution of 1N citric acid (600 ml) and brine, and dried over anhydrous sodium sulfate. The dried solution was concentrated under reduced pressure, and the residue was purified by silica gel column chromatography, giving 10 g of the objective compound.

IR (KBr, cm$^{-1}$): 1782, 1735, 1372, 1208, 1187, 1054, 700

NMR (DMSO-d$_6$, δ): 7.7 (4H, s), 6.9 (1H, s), 6.2 (1H, s), 2.32 (3H, s), 2.29 (6H, s)

Step 3

Preparation of α-aminooxy-3,4,5-triacetoxyphenylacetic acid diphenylmethyl ester.

To a solution of the product obtained in Step 2 (10 g) in dichloromethane (120 ml) was added methylhydrazine (0.83 ml) slowly at −60° C., and the mixture was stirred at 0° C. for 40 minutes. Insoluble matters were filtered off, and the filtrate was concentrated under reduced pressure. The residue was purified by silica gel column chromatography, giving 2.2 g of the objective compound.

NMR (CDCl$_3$, δ): 7.3–7.1 (12H, m), 6.9 (1H, s), 5.2 (1H, s), 2.27 (3H, s), 2.23 (6H, s)

Step 4

Preparation of 2-(2-triphenylmethylamino-4-thiazolyl)-2-[Z-[diphenylmethyloxycarbonyl-(3,4,5-triacetoxyphenyl)methyl]oxyimino]acetic acid.

To a solution of (2-triphenylmethylaminothiazolyl)-glyoxylic acid (1.7 g) in methanol (100 ml) was added dropwise a solution of the product obtained in Step 3 (2.2 g) in methanol (40 ml). The solution was stirred at room temperature for one hour, and the resulting solution was concentrated under reduced pressure. The residue was purified by silica gel column chromatography, giving 2.2 g of the objective compound.

IR (KBr, cm$^{-1}$): 1780, 1752, 1496, 1370, 1206, 1186, 1053, 701

NMR (DMSO-d$_6$, δ): 8.9 (1H, s), 7.3–7.2 (27H, m), 6.86 (1H, s), 6.83 (1H, s), 5.9 (1H, s), 2.30 (3H, s), 2.28 (6H, s)

Step 5

Preparation of (6R,7R)-7-[2-(2-triphenylmethyl-amino-4-thiazolyl)-2-[Z-[diphenylmethyloxycarbonyl-(3,4,5-triacetoxyphenyl)methyl]oxyimino]acetamido]-acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene- 2-carboxylic acid diphenylmethyl ester.

To an ice-cooled solution containing the product obtained in Step 4 (2.2 g) and (6R,7R)-7-amino-3-[(2-diphenylmethyloxycarbonyl-5-methyl-s-triazolo[1,5-a]-pyrimidin-7-yl)thiomethyl]-8-oxo-5-thia-1-azabicyclo[4.2.0]oct-2-ene-2-carboxylic acid diphenylmethyl ester (1.84 g) in dichloromethane (65 ml) was added dicyclohexylcarbodiimide (0.59 g), and the mixture was stirred overnight at room temperature. The insoluble matters were filtered off, and the filtrate was concentrated under reduced pressure The residue was dissolved in ethyl acetate and the insoluble matters were removed by filtration. The filtrate was washed with brine and dried over anhydrous sodium sulfate. The dried solution was concentrated under reduced pressure, and the residue was purified by silica gel column chromatography, giving 0.86 g (less polar form) and 0.94 g (more polar form) of the objective compound.

less polar form [(S)-isomer]

IR (KBr, cm$^{-1}$): 1782, 1742, 1521, 1508, 1498, 1371, 1185, 1054,

NMR (DMSO-d$_6$, δ): 9.6 (1H, d, J=9 Hz), 8.7 (1H, s), 7.5–7.2 (49H, m), 6.9 (1H, s), 6.83 (1H, s), 6.80 (1H, s), 5.9 (1H, s), 5.8 (1H, dd, J=5 Hz, 9 Hz), 5.2 (1H, d, J=5 Hz), 4.3 (2H, brs), 3.6 (2H, ABq), 2.6 (3H, s), 2.20 (3H, s), 2.18 (6H, s)

more polar form [(R)-isomer]

IR (KBr, cm$^{-1}$): 1782, 1742, 1596, 1498, 1450, 1371, 744, 700

NMR (DMSO-d$_6$, δ): 9.8 (1H, d, J=7 Hz), 8.9 (1H, s), 7.5–7.2 (49H, m), 6.9 (1H, s), 6.82 (1H, s), 6.76 (1H, s), 5.9 (1H, s), 5.8 (1H, dd, J=5 Hz, 7 Hz), 5.2 (1H, d, J=5 Hz), 4.3 (2H, brs), 3.6 (2H, ABq), 2.6 (3H, s), 2.3 (3H, s), 2.2 (6H, s)

Step 6

Preparation of (6R,7R)-7-[2-(2-amino-4-thiazolyl)-2-[Z-[(S)-carboxy(3,4,5-triacetoxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 5 as less polar form (0.8 g) in dichloroethane (7 ml) were added anisole (0.36 ml) and trifluoroacetic acid (0.73 ml) under ice cooling, and the resulting solution was stirred at room temperature for three hours. The solvent was removed by decantation, and the residue was washed with dichloroethane (5 ml) and crystallized with ether, giving 0.45 g of the objective compound (as trifluoroacetic acid salt).

IR (KBr, cm$^{-1}$): 1774, 1676, 1630, 1597, 1509, 1193

NMR (DMSO-d$_6$, δ): 9.5 (1H, d, J=9 Hz), 7.4 (1H, s), 7.3 (2H, s), 6.8 (1H, s), 5.8 (1H, dd, J=5, 9 Hz), 5.6 (1H, s), 5.2 (1H, d, J=5 Hz), 4.4 (2H, brs), 3.7 (2H, ABq), 2.6 (3H, s), 2.3 (9H, s)

Step 7

Preparation of the (R)-isomer of the product obtained in Example 13, Step 6.

The product obtained in Step 5 as more polar form was subjected to the same process as described in Step 6, giving 0.25 g of the objective compound.

IR (KBr, cm$^{-1}$): 1774, 1676, 1636, 1625, 1597, 1374, 1194

NMR (DMSO-D$_6$, δ): 9.8 (1H, d, J=7 Hz), 7.4 (1H, s), 7.3 (2H, s), 6.8 (1H, s), 5.8 (1H, dd, J=5, 7 Hz), 5.6 (1H, s), 5.2 (1H, d, J=5 Hz), 4.4 (2H, brs), 3.7 (2H, ABq), 2.6 (3H, s), 2.3 (9H, s)

Step 8

Preparation of (6R,7R)-7-[2-(2-amino-4-thiazolyl)-2-[Z-[(S)-carboxy(3,4,5-trihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[42.0]oct-2-ene-2-carboxylic acid.

The product obtained in Step 6 (0.43 g) was suspended in water (12 ml), and the pH of the mixture was adjusted to 8.0 with sodium bicarbonate under a nitrogen stream. After stirring at room temperature for five hours, the resulting solution was applied to a Diaion HP 10 column. The objective fractions eluted with water were collected and lyophilized, giving 0.15 g of the objective compound (as sodium salt).

IR (KBr, cm$^{-1}$): 1772, 1597, 1513, 1402, 1318

NMR (D$_2$O, δ): 7.2 (1H, s), 7.0 (1H, s), 6.6 (2H, s), 5.6 (1H, d, J=5 Hz), 5.3 (H, s), 5.0 (1H, d, J=5 Hz), 4.3 (2H, ABq), 3.4 (2H, ABq), 2.6(3H, s)

Step 9

Preparation of the (R)-isomer of the product obtained in Step 8.

The product obtained in Step 7 as more polar form was subjected to the same process as described in Step 8, giving 0.1 g of the objective compound (as sodium salt).

IR (KBr, cm$^{-1}$): 1773, 1596, 1517, 1311

NMR (D$_2$O, δ): 7.2 (1H, s), 7.0 (1H, s), 6.6 (2H, s), 5.6 (1H, d, J=4 Hz), 5.3 (1H, s), 5.0 (1H, d, J=4 Hz), 4.4 (2H, ABq), 3.3 (2H, ABq), 2.6 (3H, s)

EXAMPLE 14

Preparation of (6R,7R)-7-[2-(2-amino-4-thiazolyl)-2-[Z-[carboxy(3,4-dihydroxyphenyl)methyl]oxyimino]acetamido]-3-[(8-carboxytetrazolo[1,5-b]pyridazin-6-yl)thiomethyl]-8-oxo-5-thia-1-azabicyclo[4.2.0]oct-2-ene-2-carboxylic acid (Compound 13).

Step 1

Preparation of (6R,7R)-7-[2-(2-triphenylmethylamino-4-thiazolyl)-2-[Z-[diphenylmethyloxycarbonyl(3,4-diacetoxyphenyl)methyl]oxyimino]-acetamido]-3-[(8-diphenylmethyloxycarbonyltetrazolo[1,5-b]pyridazin-6-yl)thiomethyl]-8-oxo-5-thia-1-azabicyclo[4.2.0]oct-2-ene-2-carboxylic acid diphenylmethyl ester.

To an ice-cooled solution containing the product obtained in Step 5 of Example 8 (1.0 g) and (6R,7R)-7-amino-3-[(8-diphenylmethyloxycarbonyltetrazolo[1,5-b]pyridazin-6-yl)thiomethyl]-8-oxo-5-thia-1-azabicyclo[4.2.0]oct-2-ene-2-carboxylic acid diphenylmethyl ester (0.90 g) in dichloromethane (50 ml) was added dicyclohexylcarbodiimide (0.24 g), and the mixture was stirred overnight at room temperature. The insoluble matters were filtered off, and the filtrate was concentrated under reduced pressure The residue was redissolved in acetone and the insoluble matters were filtered off. The filtrate was concentrated under reduced pressure, and the residue was purified by silica gel column chromatography, giving 0.75 g of the objective compound.

IR (KBr, cm$^{-1}$): 1774, 1734, 1363, 1297, 1225, 1083, 700

NMR (CDCl$_3$, δ): 8.1–6.7 (55H, m), 6.1 and 6.0 (1H, s), 5.9 (1H, m), 4.9 (1H, m), 4.7 (2H, ABq), 3.2 (2H, ABq), 2.3 (6H, s)

Step 2

Preparation of (6R,7R)-7-[2-(2-amino-4-thiazolyl)-2-[Z-[carboxy(3,4-diacetoxyphenyl)-methyl]oxyimino]acetamido]-3-[(8-cartetrazolo[1,5-b]pyridazin-6-yl)thiomethyl]-8-oxo-5-thia-1-azabicyclo[4.2.0]oct-2-ene-2-carboxylic acid.

To a solution of the product obtained in Step 1 (0.75 g) in dichloroethane (3 ml) were added anisole (0.5 ml) and trifluoroacetic acid (3 ml) under ice cooling, and the resulting solution was stirred at room temperature for 3.5 hours. The resultant solution was concentrated under reduced pressure, and the residue was redissolved in dichloroethane (15 ml). The solvent was removed by decantation, and the residue was washed with dichloroethane (20 ml) and crystallized with ether, giving 0.27 g of the objective compound (as trifluoroacetic acid salt).

IR (KBr, cm$^{-1}$): 1773, 1676, 1638, 1374, 1208

NMR (DMSO-d$_6$, δ): 9.7 (1H, m), 8.1 (1H, s), 7.4–7.0 (3H, m), 6.81 and 6.76 (1H, s), 5.8 (1H, m), 5.6 (1H, s), 5.1 (1H, m), 4.3 (2H, ABq), 3.6 (2H, ABq), 2.3 (6H, s)

Step 3

Preparation of (6R,7R)-7-[2-(2-amino-4-thiazolyl)-2-[Z-[carboxy(3,4-dihydroxyphenyl)methyl]oxyimino]acetamido]-3-[(8-carboxytetrazolo[1,5-b]pyridazin-6-yl)thiomethyl]-8-oxo-5-thia-1-azabicyclo[4.2.0]oct-2-ene-2-carboxylic acid.

The product obtained in Step 2 (0.25 g) was suspended in water (6 ml), and the pH of the mixture was adjusted to 8.5 with sodium bicarbonate. The mixture was stirred under nitrogen stream at room temperature for 5 hours, and the resulting solution was applied to a Diaion HP 10 column. The objective fractions eluted with water were collected and lyophilized, giving 0.15 g of the objective compound (as sodium salt).

IR (KBr, cm$^{-1}$): 1766, 1589, 1388

NMR (D$_2$O, δ): 7.8 (1H, s), 7.2–6.8 (4H, m), 5.7 (1H, m), 5.4 (1H, s), 5.0 (1H, m), 4.1 (2H, ABq), 3.4 (2H, ABq)

EXAMPLE 15

Preparation of (6R,7R)-7-[2-(2-amino-4-thiazolyl)-2-[Z-[carboxy(3,4-dihydroxyphenyl)methyl]oxyimino]acetamido]-3-(1-pyridiniummethyl)-8-oxo-5-thia-1-azabicyclo[4.2.0]oct-2-ene-2-carboxylate (Compound 14).

Step 1

Preparation of (6R,7R)-7-[2-(2-triphenylmethylamino-4-thiazolyl)-2-[Z-[diphenylmethyloxycarbonyl(3,4-diacetoxyphenyl)methyl]oxyimino]acetamido]-3-acetoxymethyl-8-oxo-5-thia-1-azabicyclo[4.2.0]oct-2-ene-2-carboxylic acid diphenylmethyl ester.

To an ice-cooled solution containing the product obtained in Step 5 of Example 8 (3.0 g) and (6R,7R)-amino-3-acetoxymethyl-8-oxo-5-thia-1-azabicyclo[4.2.0]oct-2-ene-2-carboxylic acid diphenylmethyl ester (1.58 g) in dichloromethane (90 ml) was added dicyclohexylcarbodiimide (0.74 g), and the mixture was stirred at room temperature for 4 hours. Insoluble matters were filtered off, and the filtrate was concentrated under reduced pressure The residue was redissolved in ethyl acetate and the insoluble matters were removed by filtration. The filtrate was concentrated under reduced pressure and the residue was purified by silica gel column chromatography, giving 2.42 g of the objective compound.

NMR (DMSO-d$_6$, δ): 9.7 (1H, m), 8.9 (1H, s), 7.6–6.8 (41H, m), 5.9 (1H, s), 5.8 (1H, m), 5.2 (1H, m), 4.8 (2H, ABq), 3.6 (2H, ABq), 2.3 (3H, s), 2.2 (3H, s), 2.0 (3H, s)

Step 2

Preparation of (6R,7R)-7-[2-(2-amino-4-thiazolyl)-2-[Z-[carboxy(3,4-diacetoxyphenyl)methyl]oxyimino]acetamido]-3-acetoxymethyl-8-oxo-5-thia-1-azabicyclo[4.2.0]oct-2-ene-2-carboxylic acid.

To a solution of the product obtained in Step 1 (2.4 g) in dichloroethane (18 ml) was added anisole (1.21 ml) and trifluoroacetic acid (2.42 ml) under ice cooling, and the resulting solution was stirred at room temperature for 5 hours. The resultant solution was concentrated under reduced pressure, and the residue was crystallized with ether, giving 0.74 g of the objective compound (as trifluoroacetic acid salt).

IR (KBr, cm$^{-1}$): 1773, 1684, 1637, 1374, 1219, 1213, 1210, 1184,

NMR (DMSO-d$_6$, δ): 9.7 (1H, m), 7.4–6.8 (4H, m), 5.8 (1H, m), 5.6 (1H, s), 5.1 (1H, m), 4.8 (2H, ABq), 3.5 (2H, ABq), 2.3 (6H, s), 2.0 (3H, s)

Step 3

Preparation of (6R,7R)-7-[2-(2-amino-4- thiazolyl)-2-[Z-[carboxy(3,4-dihydroxyphenyl)-methyl]oxyimino]acetamido]-3-(1-pyridiniummethyl-8-oxo-5-thia-1-azabicyclo[4.2.0]oct-2-ene-2-carboxylate.

The product obtained in Step 2 (0.25 g) and pyridine were added to a solution of sodium iodide (0.76 g) in water (0.22 ml), and the mixture was stirred at 50° C. for 1.5 hours. Acetone (10 ml) was then added to the solution, and the formed crystals were collected by filtration. The crystals were dissolved in water, and the solution was applied to a Diaion HP 10 column. The objective fractions eluted with water were collected and lyophilized, giving 0.05 g of the objective compound.

IR (KBr, cm$^{-1}$): 1772, 1624, 1533, 1397

NMR (D$_2$O, δ): 9.0–8.0 (5H, m), 7.2–7.0 (4H, m), 5.7–5.1 (5H, m), 3.4 (2H, ABq)

Step 1

Preparation of (6R,7R)-7-[2-(2-amino-4-thiazolyl)-2-[Z-[(S)-carboxy(3,4-dihydroxyphenyl)methyl]oxyimino]acetamido]-3-(pyridiniummethyl)-8-oxo-5-thia-1-azabicyclo[4.2.0]oct-2-ene-2-carboxylate (Compound 15).

Step 1

Preparation of 2-N-phthaloyloxy-(3,4-diacetoxyphenyl)acetic acid.

To a suspension of the product obtained in Step 3 of Example 8 (102 g) in dichloroethane (150 ml) were added anisole (73 ml) and trifluoroacetic acid (140 ml) under ice cooling, and the resulting mixture was stirred at 0° C. for one hour and then at room temperature for one hour. The solvent was removed under reduced pressure, and the residue was washed with ether and hexane, then crystallized with ether, giving 59.4 g of the objective compound. NMR (DMSO-d$_6$, δ): 7.8 (4H, s), 7.5–7.2 (3H, m), 5.8 (1H, s), 2.3 (6H, s)

Step 2

Preparation of (S)-2-N-phthaloyloxy-(3,4-diacetoxyphenyl)acetic acid.

To a solution of the product obtained in Step 1 (61 g) in acetone (375 ml) was added a solution of (R)-(+)-α-methylbenzylamine (18 g) in acetone (275 ml) at once, and the resulting solution was allowed to stand at room temperature for 2.5 hours. The formed crystals were collected by filtration and washed with a small amount of acetone. The crystals were suspended in water and the pH of the suspension was adjusted to 1 with 1N hydrochloric acid. The resultant mixture was extracted twice with ethyl acetate. The organic layer was washed with water and brine, and dried over anhydrous sodium sulfate. The dried solution was concentrated under reduced pressure, and the residue was crystallized with ether and hexane, giving 12.7 g of the objective compound as milky white crystals.

NMR (CDCl$_3$, δ): 7.9–7.6 (4H, m), 7.5–7.2 (3H, m), 5.9 (1H, s), 2.28 (3H, s), 2.27 (3H, s)

Step 3

Preparation of (S)-2-N-phthaloyloxy-(3,4-diacetoxyphenyl)acetic acid diphenylmethyl ester.

To an ice-cooled solution of the product obtained in Step 2 (22 g) in ethyl acetate (600 ml) was added a solution of diphenyldiazomethane (27.9 g) in ethyl acetate (150 ml), and the resulting solution was stirred at room temperature for one hour. The solvent was then removed under reduced pressure, and the residue was washed with hexane and purified by silica gel column chromatography, giving 26.3 g of the objective compound as colorless crystals.

NMR (CDCl$_3$, δ): 7.8–7.6 (4H, m), 7.4–6.9 (14H, m), 6.0 (1H, s), 2.3 (6H, s)

Step 4

Preparation of (S)-2-aminooxy-(3,4-diacetoxyphenyl)acetic acid diphenylmethyl ester.

To a solution of the product obtained in Step 3 (26.3 g) in dichloromethane (370 ml) was added methylhydrazine (2.41 ml) slowly at −30° C. The mixture was left to stand until it reached room temperature, and stirring for three hours. The insoluble matters were filtered off, and the filtrate was concentrated under reduced pressure The residue was purified by silica gel column chromatography, giving 20 g of the compound as pale yellow oil.

NMR (CDCl$_3$, δ): 7.3–6.9 (14H, m), 5.2 (1H, s), 2.3 (6H, s)

Step 5

Preparation of 2-(2-amino-4-thiazolyl)-2-[Z-[(S)-diphenylmethyloxycarbonyl(3,4-diacetoxyphenyl)methyl]oxyimino]acetic acid.

To an ice-cooled solution of the product obtained in Step 4 (20.3 g) in dimethylformamide (60 ml) was added 2-(2-amino-4-thiazolyl)glyoxylic acid (7.8 g). The mixture was allowed to stand until it reached room temperature, and stirred overnight. The reaction mixture was then poured into ice-cooled water (400 ml), and the pH of the resulting mixture was adjusted to 2.0 with 1N hydrochloric acid. The mixture was extracted twice with ethyl acetate (500 ml). The combined organic layer was washed with brine (200 ml) and dried over anhydrous sodium sulfate. The dried solution was concentrated under reduced pressure and the residue was dissolved in a small amount of chloroform. This solution was added dropwise to ether. The formed crystals were collected by filtration and washed with ether, giving 22.3 g of the objective compound as pale yellow crystals.

NMR (DMSO-d$_6$, δ): 7.4–6.7 (15H, m), 6.0 (1H, s), 2.3 (6H, s)

Step 6

Preparation of (6R,7R)-7-[2-(2-amino-4-thiazolyl)-2-[Z-[(S)-diphenylmethyloxycarbonyl(3,4-diacetoxyphenyl)methyl]oxyimino]acetamido]3-chloromethyl-8-oxo-5-thia-1-azabicyclo[4.2.0]oct-2-ene-2-carboxylic acid p-methoxybenzyl ester.

To a suspension containing the product obtained in Step 5 (21.8 g) and (6R,7R)-7-amino-3-chloromethyl-8-oxo-5-thia-1-azabicyclo[4.2.0]oct-2-ene-2-carboxylic acid p-methoxybenzyl ester p-toluenesulfonate (19.5 g) in dry dichloromethane (250 ml) were added dicyclohexylamine (7.2 ml) and diethylaniline (11.5 ml), and the mixture was cooled to −15° C. A solution of phosphorus oxychloride (3.4 ml) in dry dichloromethane (30 ml) was added dropwise to the suspension over a period of 40 minutes, and the mixture was stirred for 1.5 hours at −15° C. Ethyl acetate (1 liter) was added, and the mixture was washed twice with 1N hydrochloric acid (300 ml), twice with saturated sodium bicarbonate solution (200 ml), then once with brine (300 ml), and dried over anhydrous sodium sulfate. The dried solution was concentrated under reduced pressure, and the residue was crystallized with ether, giving 29.9 g of the objective compound as pale yellow crystals.

NMR (DMSO-d$_6$, δ): 9.7 (1H, d, J=7 Hz), 7.5–6.8 (19H, m), 5.9 (1H, s), 5.8 (1H, dd, J=5, 7 Hz), 5.2 (2H, brs), 5.1 (1H, d, J=5 Hz), 4.5 (2H, brs), 3.7 (3H, s), 3.5 (2H, ABq), 2.3 (6H, s)

Step 7

Preparation of (6R,7R)-7-[2-(2-amino-4-thiazolyl)-2-[Z-[(S)-diphenylmethyloxycarbonyl-(3,4-diacetoxyphenyl)methyl]oxyimino]acetamido]-3-iodomethyl-8-oxo-5-thia-1-azabicyclo[4.2.0]oct-2-ene-2-carboxylic acid p-methoxybenzyl ester.

To a solution of the product obtained in Step 6 (14 g) in acetone (210 ml) was added sodium iodide (4.85 g) in total darkness and the mixture was stirred at room temperature for one hour. The reaction mixture was then poured into water (300 ml) and extracted twice with ethyl acetate (500 ml). The combined organic layer was washed with 5% sodium thiosulfate solution (200 ml) and brine (200 ml), and dried over anhydrous sodium sulfate. The dried solution was concentrated under reduced pressure, giving 15.1 g of the objective compound as yellow crystals.

NMR (DMSO-d$_6$, δ): 9.7 (1H, d, J=9 Hz), 7.4–6.8 (19H, m), 5.9 (1H, m), 5.8 (1H, dd, J=5, 9 Hz), 5.2 (2H, brs), 5.1 (1H, d, J=5 Hz), 4.3 (2H, brs), 3.7 (3H, s), 3.6 (2H, ABq), 2.3 (6H, s)

Step 8

Preparation of (6R,7R)-7-[2-(2-amino-4-thiazolyl)-2-[Z-[(S)-diphenylmethyloxycarbonyl-(3,4-diacetoxyphenyl)methyl]oxyimino]acetamido]-3-(pyridiniummethyl)-8-oxo-5-thia-1-azabicyclo-[4.2.0]oct-2-ene-2-carboxylic acid p-methoxybenzyl ester iodide.

To an ice-cooled solution of the product obtained in Step 7 (15.1 g) in the mixture of dry dichloromethane (50 ml) and dry dimethyl sulfoxide (50 ml) was added dropwise a solution of pyridine (1.17 ml) in dry dichloromethane (10 ml) over a period of 30 minutes, and the reaction mixture was stirred at 0° C. for 5 minutes, then at room temperature for 1.5 hours. The resulting solution was poured into ether (1.5 liters) and the solvent was removed by decantation. The residue was crystallized with ether (1 liter), giving 13.5 g of the objective compound as yellow crystals.

NMR (DMSO-d$_6$, δ): 9.7 (1H, d, J=9 Hz), 9.0 (2H, m), 8.7 (1H, m), 8.2 (2H, m), 7.4–6.8 (19H, m), 5.9 (1H, s), 5.8 (1H, dd, J=5, 9 Hz), 5.6 (2H, brs), 5.2 (2H, brs), 5.1 (1H, d, J=5 Hz), 3.7 (3H, s), 3.6 (2H, ABq), 2.3 (3H, s), 2.2 (3H, s)

Step 9

Preparation of (6R,7R)-7-[2-(2-amino-4-thiazolyl)-2-[Z-[(S)-carboxy(3,4-diacetoxyphenyl)methyl]oxyimino]acetamido]-3-(pyridiniummethyl)-8-oxo-5-thia-1-azabicyclo[4.2.0]oct-2-ene-2-carboxylate.

To a solution of the product obtained in Step 8 (13.4 g) in dichloroethane (86 ml) were added anisole (10.7 ml) and trifluoroacetic acid (21.4 ml) under ice cooling, and the mixture was stirred at room temperature for 3.5 hours. The resulting solution was poured into ether (4 liter), and the formed crystals were collected by filtration, giving 9.8 g of the objective compound (as trifluoroacetic acid salt). 9.5 (1H, d, J=9 Hz), 9.0 (2H, m), 8.7 (1H, m), 8.2 (2H, m), 7.4–6.8 (4H, m), 5.8 (1H, dd, J=5, 9 Hz), 5.60 (2H, brs), 5.58 (1H, s), 5.2 (1H, d), 3.4 (2H, ABq), 2.27 (3H, s), 2.24 (3H, s)

Step 10

Preparation of (6R,7R)-7-[2-(2-amino-4-thiazolyl)-2-[Z-[(S)-carboxy(3,4-dihydroxyphenyl)methyl]ox-yimino]acetamido]-3-(pyridiniummethyl)-8-oxo-5-thia-1-azabicyclo[4.2.0]oct-2-ene-2-carboxylate.

The product obtained in Step 9 (9.8 g) was suspended in water (255 ml) and the pH of the mixture was adjusted to 8.0–8.5 with sodium bicarbonate under a nitrogen stream. The mixture was stirred overnight at room temperature, and the resulting solution was applied to a Diaion HP 10 column. The objective fractions eluted with 20% methanol in water were collected, concentrated to one third of its original volume under reduced pressure, and then lyophilized, giving 2.88 g of the objective compound (as sodium salt).

IR (KBr, cm$^{-1}$): 773, 1624, 1609, 1533, 1389

NMR (D$_2$O, δ): 8.9 (2H, m), 8.5 (1H, m), 8.0 (2H, m), 6.9–6.7 (4H, m), 5.7 (1H, d, J=5 Hz), 5.4 (1H, s), 5.3 (2H, ABq), 5.1 (1H, d, J=5 Hz), 3.1 (2H, ABq)

EXAMPLE 17

Preparation of (6R,7R)-7-[2-(2-amino-4-thiazolyl)-2-[Z-[(S)-carboxy(3,4-dihydroxyphenyl)methyl]ox-yimino]acetamido]-3-(2,3-cyclopentenopyridiniumme-thyl)-8-oxo-5-thia-1-azabicyclo[4.2.0]oct-2-ene-2-carboxylate (Compound 16).

Step 1

Preparation of (6R,7R)-7-[2-(2-amino-4-thiazolyl)-2-[Z-[(S)-diphenylmethyloxycarbonyl(3,4-diacetoxy-phenyl)methyl]oxyimino]acetamido]-3-(2,3-cyclopen-tenopyridiniummethyl)-8-oxo-5-thia-1-azabicyclo[4.2.-0]oct-2-ene-2-carboxylic acid p-methoxybenzyl ester iodide.

To an ice-cooled solution of the product obtained in Step 7 of Example 16 (16 g) in the mixture of dry dichloromethane (50 ml) and dry dimethyl sulfoxide (50 ml) was added dropwise a solution of 2,3-cyclopentenopyri-dine (1.81 g) in dry dichloromethane (10 ml) over a period of 30 minutes, and the solution was stirred at 0° C. for 5 minutes, then at room temperature for 2.5 hours. The resulting solution was poured into ether (2 liters) and the solvent was removed by decantation. The residue was crystallized with ether (1 liter), giving 14.5 g of the objective compound as yellow crystals.

NMR (DMSO-D$_6$, δ): 9.7 (1H, d, J=8 Hz), 8.4 (2H, m), 7.9 (1H, m), 7.4–6.7 (19H, m), 5.90 (1H, dd, J=5, 8 Hz), 5.87 (1H, s), 5.5 (2H, brs), 5.2 (2H, brs), 5.1 (1H, d, J=5 Hz), 3.7 (3H, s), 3.5–3.1 (6H, m), 2.26 (3H, s), 2.23 (3H, s), 2.20 (2H, m)

Step 2

Preparation of (6R,7R)-7-[2-(2-amino-4-thiazolyl)-2-[Z-[(S)-carboxy(3,4-diacetoxyphenyl)methyl]ox-yimino]acetamido]-3-(2,3-cyclopentenopyridiniumme-thyl)-8-oxo-5-thia-1-azabicyclo[4.2.0]oct-2-ene-2-carboxylate.

To a solution of the product obtained in Step 1 (14.5 g) in dichloroethane (95 ml) were added anisole (11.6 ml) and trifluoroacetic acid (23.2 ml) under ice cooling, and the mixture was stirred at 0° C. for 5 minutes, then at room temperature for 3 hours. The resulting solution was poured into ether (4 liters), and the formed crystals were collected by filtration, giving 10.8 g of the objective compound (as trifluoroacetic acid salt).

NMR (DMSO-d$_6$, δ): 9.5 (1H, d, J=8 Hz), 8.6 (1H, m), 8.4 (1H, m), 7.9 (1H, m), 7.4–6.8 (4H, m), 5.9 (1H, dd, J=5, 8 Hz), 5.6 (1H, s), 5.4 (2H, brs), 5.1 (1H, d), 3.4–3.0 (6H, m), 2.27 (3H, s), 2.24 (3H, s), 2.20 (2H, m)

Step 3

Preparation of (6R,7R)-7-[2-(2-amino-4-thiazolyl)-2-[Z-[(S)-carboxy(3,4-dihydroxyphenyl)methyl]ox-yimino]acetamido]-3-(2,3-cyclopentenopyridiniumme-thyl)-8-oxo-5-thia-1-azabicyclo[4.2.0]oct-2-ene-2-carboxylate.

The product obtained in Step 2 (10.8 g) was suspended in water (270 ml), and the pH of the mixture was adjusted to 8.0–8.5 with sodium bicarbonate under a nitrogen stream. The mixture was stirred overnight at room temperature, and the resulting solution was applied to a Diaion HP 10 column. The objective fractions eluted with 20% methanol in water were collected, concentrated to one third of its original volume under reduced pressure, and lyophilized, giving 2.49 g of the objective compound (as sodium salt).

IR (KBr, cm$^{-1}$): 1774, 1623, 1610, 1606, 1529, 1390

NMR (D$_2$O, δ): 8.5 (1H, m), 8.2 (1H, m), 7.7 (1H, m), 7.0–6.7 (4H, m), 5.7 (1H, d, J=5 Hz), 5.4 (1H, s), 5.3 (2H, brs), 5.0 (1H, d, J=5 Hz), 3.4–2.1 (8H, m)

EXAMPLE 18

Preparation of (6R,7R)-7-[2-(2-amino-4-thiazolyl)-2-(3,4-dihydroxybenzoylamino)-acetamido]-3-[(2-car-boxy-5-methyl-s-triazolo[1,5-a]pyrimidin-7-yl)thiome-thyl]-8-oxo-5-thia-1-azabicyclo[4.2.0]oct-2-ene-2-carboxylic acid (Compound 17)

Step 1

Preparation of (6R,7R)-7-[2-(t-butyloxycar-bonylamino)-2-triphenylmethylamino-4-thiazolyl-)acetamido]-3-[(2-diphenylmethyloxycarbonyl-5-meth-yl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a solution of 2-(t-buthyloxycarbonylamino)-2-(2-triphenylmethylamino-4-thiazolyl)acetic acid (6.83 g) in dimethylformamide (20 ml) was added a solution of (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (10 g) in dichloromethane (200 ml). Dicyclohexylcarbodiimide (2.73 g) was added to the solution under ice cooling and the mixture was stirred at room temperature for one hour. The insoluble matters were filtered off, and the filtrate was concentrated under reduced pressure. The residue was redissolved in ethyl acetate and the insoluble matters were removed by filtration. The filtrate was washed with brine and dried over anhydrous sodium sulfate. The dried solution was concentrated under reduced pressure, and the residue was purified by silica gel column chromatography, giving 10.8 g of the objective compound.

NMR (DMSO-d$_6$, δ): 8.5 (1H, m), 8.3 (1H, m), 7.5–7.1 (37H, m), 7.0 (1H, s), 6.4 (1H, s), 5.8 (1H, m), 5.2 (1H, d, J=5 Hz), 5.0 (1H, m), 4.3 (2H, brs), 3.7 (2H, ABq), 2.6 (3H, s), 1.4 (9H, s)

Step 2

Preparation of (6R,7R)-7-[2-amino-2-(2--triphenylmethylamino-4-thiazolyl)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of the product obtained in Step 1 (1 g) in dry dichloromethane was added 3 ml of methanol saturated with hydrogen chloride, and the mixture was stirred for 15 minutes. The resulting solution was poured into saturated aqueous sodium bicarbonate solution, and extracted with dichloromethane. The organic layer was washed with brine, dried over anhydrous sodium sulfate, and concentrated under reduced pressure. The residue was purified by silica gel column chromatography, giving 0.8 g of the objective compound.

IR (KBr, cm$^{-1}$): 1787, 1737, 1596, 1507, 1498, 1222, 1202, 1183, 755, 700

NMR (DMSO-d$_6$, $\delta$): 8.5 (1H, m), 7.5–7.2 (37H, m), 7.0 (1H, s), 6.4 (1H, s), 5.9–5.1 (3H, m), 4.3 (2H, brs), 3.7 (2H, ABq), 2.6 (3H, s)

Step 3

Preparation of (6R,7R)-7-[2-(3,4-diacetoxybenzoylamino)-2-(2-triphenylmethylamino-4-thiazolyl)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a solution of the product obtained in Step 2 (0.75 g) in dry dichloromethane (10 ml) was added bis(trimethylsilyl)acetamide (0.32 ml) and the mixture was stirred for 30 minutes. Then a solution of 3,4-diacetoxybenzoyl chloride (0.17 g) in dry dichloromethane (5 ml) was added dropwise at $-10°$ C. The resulting solution was stirred for one hour and concentrated under reduced pressure. The residue was dissolved in ethyl acetate (120 ml), and the solution was washed twice with brine and dried over anhydrous sodium sulfate. The dried solution was concentrated under reduced pressure, giving 0.7 g of the objective compound as pale yellow crystals.

IR (KBr, cm$^{-1}$): 1780, 1741, 1508, 1497, 1372, 1205, 1182, 700

NMR (DMSO-d$_6$, $\delta$): 9.0 (1H, d, J=7 Hz), 8.5 (1H, s), 8.2–7.1 (40H, m), 6.9 (1H, s), 6.5 (1H, s), 5.8–5.1 (3H, m), 4.3 (2H, brs), 3.7 (2H, ABq), 2.6 (3H, s), 2.3 (6H, s)

Step 4

Preparation of (6R,7R)-7-[2-(2-amino-4-thiazolyl)-2-(3,4-diacetoxybenzoylamino)-acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

To a solution of the product obtained in Step 3 (0.65 g) in dichloroethane (2 ml) were added anisole (0.5 ml) and trifluoroacetic acid (1 ml) under ice cooling, and the resulting solution was stirred at room temperature for 2 hours. The solvent was removed by decantation, and the residue was washed with a small amount of dichloroethane and crystallized with ether, giving 0.31 g of the objective compound as pale yellow crystals (as trifluoroacetic acid salt).

IR (KBr, cm$^{-1}$): 1774, 1654, 1647, 1509, 1205

NMR (DMSO-D$_6$, $\delta$): 9.2 (1H, d), 8.9–8.8 (1H, m), 7.9–7.3 (4H, m), 6.6 (1H, s), 5.8–5.6 (2H, m), 5.1 (1H, d, J=4 Hz), 4.4 (2H, brs), 3.7 (2H, ABq), 2.6 (3H, s), 2.3 (6H, s)

Step 5

Preparation of (6R,7R)-7-[2-(2-amino-4-thiazolyl)-2-(3,4-dihydroxybenzoylamino)acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The product obtained in Step 4 (0.28 g) was suspended in water (10 ml), and the pH of the mixture was adjusted to 8 with sodium bicarbonate. The mixture was stirred at room temperature for 3 hours, and the resulting solution was applied to a Diaion HP 10 column. The objective fractions eluted by 17% methanol in water were collected, concentrated to one third of its original volume under reduced pressure, then lyophilized, giving 0.16 g of the objective compound (as sodium salt).

IR (KBr, cm$^{-1}$): 1763, 1624, 1599, 1514, 1406, 1352, 1314

NMR (DMSO-d$_6$, $\delta$): 9.0 (1H, m), 8.1 (1H, m), 7.6 (1H, s), 7.3–6.7 (3H, m), 6.4 (1H, s), 5.7–5.5 (2H, m), 5.1–4.9 (1H, m), 4.6 (2H, ABq), 3.6 (2H, ABq), 2.5 (3H, s)

Table 5 lists structures of Compounds 19 to 91 together with their spectral data. All of these compounds have been prepared by the methods described in Examples 1 to 18. These methods can be divided into five groups according to the similarities in reaction procedures. Table 4 shown below gives the groups of examples, and compounds which have been prepared by the method employed by these groups of examples.

TABLE 4

| Group | Example | Compound |
|---|---|---|
| 1 | 2, 4 | 19–33, 35–44, 46, 48, 51–54 |
| 2 | 1, 3, 5 | 34, 45, 47, 49, 50, 55 |
| 3 | 6, 8 | 56–66, 68, 70–72 |
| 4 | 7, 9–17 | 67, 69, 73–89 |
| 5 | 18 | 90, 91 |

TABLE 5

[Structure shown: cephalosporin-type compound with aminothiazole group, oxime linker (O)ₐ-C(R²)ᵦ-C(R³)(R⁴)ᵧ-X, CONH to β-lactam with S-CH₂Y side chain and COOH]

| Example No. | X | Y | R² | R³ | R⁴ | R⁵ | a | b | c | a bond of ( \| ) | IR (cm⁻¹) | NMR (δ) |
|---|---|---|---|---|---|---|---|---|---|---|---|---|
| 19 (CF₃COOH salt) | [2-methylphenyl with OCOCH₃] | [triazolopyrimidine with COOH, CH₃, SCH₃] | O | — | | | 1 | 1 | 0 | double bond | 1768, 1685, 1604, 1597, 1240, 1196. | (DMSO—d₆); 10.0(1H, d, J=8Hz), 7.9–7.2(5H, m), 7.1(1H, s), 5.9(1H, dd, J=5, 8Hz), 5.3(1H, d, J=5Hz), 4.4(2H, brs), 3.6(2H, ABq), 2.6(3H, s), 2.3(3H, s) |
| 20 (CF₃COOH salt) | [3-methylphenyl with OCOCH₃] | [triazolopyrimidine with COOH, CH₃, SCH₃] | O | — | | | 1 | 1 | 0 | double bond | 1772, 1763, 1735, 1684, 1640, 1596, 1509, 1260, 1203. | (DMSO—d₆); 10.0(1H, d, J=7Hz), 7.7–7.3(5H, m), 7.1(1H, s), 5.9(1H, dd, J=5, 7Hz), 5.2(1H, d, J=5Hz), 4.4(2H, brs), 3.7(2H, ABq), 2.6(3H, s), 2.3(3H, s) |

TABLE 5-continued

| | | | | | | |
|---|---|---|---|---|---|---|
| 21 (CF₃COOH salt) | [phenyl-OCOCH₃] | [pyrazole-COOH-pyrimidine-CH₃ with S] | 0 | — | 1 1 0 double bond | 1773, 1757, 1752, 1736, 1600, 1509, 1250, 1199, 1164. | (DMSO—d₆); 10.1(1H, d, J=8Hz), 8.1(2H, d), 7.4(1H, s), 7.3(2H, d), 7.1(1H, s), 6.0(1H, dd, J=5, 8Hz), 5.3(1H, d, J=5Hz), 4.5(2H, brs), 3.7(2H, ABq), 2.6(3H, s), 2.3(3H, s) |
| 22 (CF₃COOH salt) | [phenyl-NO₂] | [pyrazole-COOH-pyrimidine-CH₃ with S] | 0 | — | 1 1 0 double bond | 1778, 1684, 1637, 1597, 1527, 1523, 1509, 1250. | (DMSO—d₆); 10.1(1H, d, J=8Hz), 8.4-8.2(4H, m),7.4(1H, s), 7.2(1H, s), 6.0(1H, dd, J=5, 8Hz), 5.3(1H, d, J=5Hz), 4.4(2H, brs), 3.7(2H, ABq), 2.6(3H, s) |
| 23 (CF₃COOH salt) | [phenyl-SO₂CH₃] | [pyrazole-COOH-pyrimidine-CH₃ with S] | 0 | — | 1 1 0 double bond | 1772, 1764, 1735, 1685, 1637, 1597, 1509, 1299, 1249. | (DMSO—d₆); 10.1(1H, d, J=8Hz), 8.3-8.0(4H, m), 7.4(1H, s), 7.2(1H, s), 6.0(1H, dd, J=5, 8Hz), 5.3(1H, d, J=5Hz), 4.5(2H, brs), 3.3(3H, s), 2.6(3H, s) |
| 24 (CF₃COOH salt) | [phenyl-NHCOCH₃, NHCOCH₃] | [pyrazole-COOH-pyrimidine-CH₃ with S] | 0 | — | 1 1 0 double bond | 1780, 1684, 1597, 1509, 1228, 1191. | (DMSO—d₆); 10.0(1H, d, J=9Hz), 9.6(1H, s), 9.5(1H, s), 8.1-7.8(3H, m), 7.4(1H, s), 7.1(1H, s), 6.0(1H, dd, J=5, 9Hz), 5.3(1H, d, J=5Hz), 4.5(2H, s), 3.7(2H, ABq), 2.6(3H, s), 2.1(3H, s), 2.0(3H, s) |

TABLE 5-continued

| | Structure 1 | Structure 2 | col | col | col | IR | NMR |
|---|---|---|---|---|---|---|---|
| 25 (CF₃COOH salt) | Cl-phenyl-Cl | pyrazolo-pyrimidine COOH, CH₃, S- | O | — | 1 1 0 | double bond | 1773, 1764, 1684, 1637, 1596, 1509, 1268, 1233. | (DMSO—d₆); 10.2(1H, d, J=8Hz), 8.1–7.8(3H, m), 7.4(1H, s), 7.2(1H, s), 6.0(1H, dd, J=5, 8Hz), 5.3(1H, d, J=5Hz), 4.5(2H, brs), 3.7 (2H, ABq), 2.6(3H, s) |
| 26 (CF₃COOH salt) | phenyl-OC₂H₅, OC₂H₅ | pyrazolo-pyrimidine COOH, CH₃, S- | O | — | 1 1 0 | double bond | 1780, 1774, 1739, 1735, 1597, 1509, 1268, 1246, 1201. | (DMSO—d₆); 10.1(1H, d, J=8Hz), 7.6–7.1(5H, m), 6.0(1H, dd, J=5, 8Hz), 5.3(1H, d, J=5Hz), 4.6(2H, brs), 4.22(2H, q, J=5Hz), 4.18 (2H, q, J=5Hz), 3.8(2H, ABq), 2.6(3H, s), 1.34(3H, t, J=5Hz), 1.32(3H, t, J=5Hz) |
| 27 (CF₃COOH salt) | phenyl-O—CH₂—CH₂—O (dioxane fused) | pyrazolo-pyrimidine COOH, CH₃, S- | O | — | 1 1 0 | double bond | 1774, 1637, 1610, 1596, 1509, 1293. | (DMSO—d₆); 10.1(1H, d, J=8Hz), 7.7–7.3(4H, m), 7.1(1H, s), 6.0(1H, dd, J=5, 8Hz), 5.2 (1H, d, J=5Hz), 4.5(2H, brs), 4.3(4H, s), 3.8(2H, ABq), 2.6(3H, s) |
| 28 (CF₃COOH salt) | phenyl-OSO₂CH₃, OSO₂CH₃ | pyrazolo-pyrimidine COOH, CH₃, S- | O | — | 1 1 0 | double bond | 1771, 1686, 1638, 1596, 1511, 1371, 1256, 1178, 1099. | (DMSO—d₆); 10.1(1H, d, J=7Hz), 8.1–7.7(3H, m), 7.4(1H, s), 7.2(1H, s), 6.0(1H, dd, J=5, 7Hz), 5.3(1H, d, J=5Hz), 4.4(2H, brs), 3.7 ABq), 3.6(3H, s), 3.5(3H, s), 2.6(3H, s) |

TABLE 5-continued

| | | | | | IR | NMR |
|---|---|---|---|---|---|---|
| 29 (CF₃COOH salt) | [phenyl with OCOC₃H₇, OCOC₃H₇, CH₃ substituents] | [bicyclic structure with COOH, N, N, N, CH₃, S] | O | — | 1 1 0 double bond | 1771, 1764, 1736, 1597, 1509, 1279, 1260, 1170, 1111. | (DMSO—d₆); 10.2(1H, d, J=8Hz), 8.1-7.1(5H, m), 5.9(1H, dd, J=5, 8Hz), 5.3(1H, d, J=5Hz), 4.5(2H, brs), 3.7(2H, ABq), 2.6(11H, brs) 1.1(6H, t, J=7Hz) |
| 30 (CF₃COOH salt) | [phenyl with OCH₃, OCOCH₃, CH₃ substituents] | [bicyclic structure with COOH, N, N, N, CH₃, S] | O | — | 1 1 0 double bond | 1764, 1737, 1690, 1642, 1598, 1509, 1286, 1219, 1197, 1168. | (DMSO—d₆); 10.1(1H, d, J=8Hz), 7.7(1H, d, J=8Hz), 7.6(1H, s), 7.4(1H, d, J=8Hz), 7.2(1H, d, J=8Hz), 7.1(1H, s), 5.9(1H, dd, J=5, 8Hz), 5.2(1H, d, J=5Hz), 4.4(2H, brs), 3.9(3H, s), 3.7(2H, ABq), 2.6(3H, s), 2.3(3H, s) |
| 31 (CF₃COOH salt) | [phenyl with OCOCH₂Cl, OCOCH₂Cl, CH₃ substituents] | [bicyclic structure with COOH, N, N, N, CH₃, S] | O | — | 1 1 0 double bond | 1779, 1685, 1637, 1596, 1508, 1279, 1260, 1169, 1118. | (DMSO—d₆); 10.1(1H, d, J=8Hz), 8.1-7.1(5H, m), 5.9(1H, dd, J=5, 8Hz), 5.3(1H, d, J=5Hz), 4.8(2H, s), 4.7(2H, s), 4.5(2H, brs), 3.7(2H, ABq), 2.6(3H, s), |
| 32 (CF₃COOH salt) | [phenyl with OCOCH₃, OCOCH₃, CH₃ substituents] | [bicyclic structure with COOH, N, N, N, CH₃, S] | O | — | 1 1 0 double bond | 1773, 1763, 1752, 1686, 1637, 1509, 1200. | (DMSO—d₆); 10.0(1H, d, J=8Hz), 8.0(1H, d, J=9Hz), 7.4-7.1(4H, m), 5.9 (1H, dd, J=5, 8 Hz), 5.2(1H, d, J=5Hz), 4.4(2H, brs), 3.7 (2H, ABq) 2.6(3H, s) 2.3(3H, s) |

TABLE 5-continued

| | Ar | Structure | | | IR / NMR |
|---|---|---|---|---|---|
| 33 (CF₃COOH salt) | 4-methyl-2-(acetoxy)phenyl (catechol carbonate-like) | COOH-pyrazolo-pyrimidine with SCH₃ | O | — 1 1 0 double bond | 1839, 1773, 1735, 1685, 1637, 1597, 1509, 1269, 1249, 1186. (DMSO—d₆); 10.1(1H, d, J=8Hz), 8.3-7.6(3H, m), 7.4(1H, s), 7.2(1H, s), 6.1(1H, dd, J=5, 8Hz), 5.3(1H, d, J=5Hz), 4.4(2H, brs), 3.8(2H, ABq), 2.6(3H, s). |
| 34 | 2,4-dihydroxyphenyl | COOH-pyrazolo-pyrimidine with SCH₃ | O | — 1 1 0 double bond | 1773, 1735, 1654, 1598, 1509, 1298. (DMSO—d₆); 10.1(1H, d, J=8Hz), 7.4-6.8(5H, m), 5.9(1H, dd, J=5, 8Hz), 5.3(1H, d, J=5 Hz), 4.5(2H, brs), 3.7(2H, ABq), 2.6(3H, s) |
| 35 (CF₃COOH salt) | 3-nitro-4,5-bis(acetoxy)phenyl | COOH-pyrazolo-pyrimidine with SCH₃ | O | — 1 1 0 double bond | 1780, 1685, 1637, 1597, 1545, 1509, 1292, 1192, 1143. (DMSO—d₆); 10.1(1H, d, J=8Hz), 8.8(1H, d, J=2Hz), 8.4(1H, d, J=2Hz), 7.4(1H, s), 7.2 (1H, s), 6.0(1H, dd, J=5, 8Hz), 5.3(1H, d, J=5Hz), 4.5(2H, brs), 3.7(2H, ABq), 2.6(3H, s), 2.4(3H, s), 2.3(3H, s). |
| 36 (CF₃COOH salt) | 3-methyl-4,5-bis(acetoxy)phenyl | COOH-pyrazolo-pyrimidine with SCH₃ | O | — 1 1 0 double bond | 1775, 1686, 1638, 1597, 1510, 1205, 1158. (DMSO—d₆); 10.1(1H, d, J=8Hz), 7.8(1H, s), 7.7(1H, s), 7.4(1H, s), 7.1(1H, s), 6.0(1H, dd, J=5, 8Hz), 5.3(1H, d, J=5Hz), 4.5(2H, brs), 3.7 (2H, ABq), 2.6(3H, s), 2.4(2H, s), 2.3(3H, s)2.2(3H, s) |

TABLE 5-continued

| | | | 1,1,0 double bond | | |
|---|---|---|---|---|---|
| 37 (CF₃COOH salt) | ![structure: benzene ring with OCOCH₃, OCOCH₃, H₃C substituents] | ![structure: pyrazolopyrimidine with COOH, CH₃, S-] | — 1 1 0 double bond | 1772, 1685, 1598, 1509, 1251, 1203, 1165. | (DMSO—d₆); 10.1(1H, d, J=8Hz), 7.8(1H, d, J=9Hz), 7.4(1H, s), 7.3(1H, d, J=9Hz), 7.1 (1H, s), 5.8(1H, dd, J=5, 8Hz), 5.2(1H, d, J=5Hz), 4.4(2H, brs), 3.6(2H, ABq), 2.6(3H, s) 2.34(3H, s), 2.33(3H, s), 2.27(3H, s) |
| 38 (CF₃COOH salt) | ![structure: benzene ring with OCOCH₂Cl, OCOCH₂Cl substituents] | ![structure: pyrazolopyrimidine with COOH, CH₃, S-] | — 1 1 0 double bond | 1781, 1637, 1597, 1598, 1509, 1324, 1234, 1170, 1128. | (DMSO—d₆); 10.1(1H, d, J=8Hz), 8.0(2H, s), 7.4(1H, s), 7.2(1H, s), 5.9(1H, dd, J=5, 8 Hz), 5.3(1H, d, J=5Hz), 4.8(2H, s), 4.7(4H, s), 4.5(2H, brs), 3.7(2H, ABq), 2.6(3H, s). |
| 39 (CF₃COOH salt) | ![structure: benzene ring with OCH₃, OCOCH₃ substituents] | ![structure: pyrazolopyrimidine with COOH, CH₃, S-] | — 1 1 0 double bond | 1774, 1685, 1637, 1598, 1509, 1340, 1196, 1164, 1097. | (DMSO—d₆); 10.1(1H, d, J=8Hz), 7.5(2H, s), 7.4(1H, s), 7.1(1H, s), 5.9(1H, dd, J=5, 8 Hz), 5.2(1H, d, J=5Hz), 4.5(2H, brs), 3.9 (3H, s), 3.7(2H, ABq), 2.6(3H, s), 2.31(3H, s), 2.27(3H, s) |
| 40 (CF₃COOH salt) | ![structure: benzene ring with OCOCH₃, OCOCH₃, H₃COCO substituents] | ![structure: pyrazolopyrimidine with COOH, CH₃, S-] | — 1 1 0 double bond | 1781, 1685, 1637, 1597, 1509, 1260, 1181. | (DMSO—d₆); 10.1(1H, d, J=7Hz), 7.9(1H, d, J=9Hz), 7.4(1H, s), 7.2(1H, d, J=9Hz), 7.1 (1H, s), 5.9(1H, dd, J=5, 7Hz), 5.2(1H, d, J=5Hz), 4.4(2H, brs), 3.7(2H, ABq), 2.6(3H, s), 2.3(9H, s) |

| | | | | |
|---|---|---|---|---|
| 41 (CF₃COOH salt) | Ar with OCOCH₃, OCOCH₃, H₃COCO substituents on benzene ring | Pyrimidine with COOH, CH₃, -S- linkage; double bond | — 1 1 0 double bond | O | 1774, 1685, 1676, 1654, 1598, 1509, 1199, 1162, 1124. | (DMSO-d₆); 10.0(1H, d, J=8Hz), 7.8(1H, s), 7.42(1H, s), 7.37(1H, s), 7.1(1H, s), 5.9(1H, dd, J=5, 8Hz), 5.2(1H, d, J=5Hz), 4.5(2H, brs), 3.7(2H, ABq), 2.6(3H, s), 2.30(6H, s) 2.27(3H, s) |
| 42 (CF₃COOH salt) | Ar with COOCH₂Cl, OCOCH₂Cl, H₃C substituents | Pyrimidine with COOH, CH₃, -S- linkage; double bond | — 1 1 0 double bond | O | 1781, 1685, 1597, 1509, 1201, 1182, 1125. | (DMSO-d₆); 10.1(1H, d, J=9Hz), 7.8(1H, s), 7.4(2H, s), 7.1(1H, s), 5.9(1H, dd, J=5, 9 Hz), 5.2(1H, d, J=5Hz), 4.7(2H, s), 4.6(2H, s), 4.5(2H, brs), 3.7(2H, ABq), 2.6(3H, s), 2.5(3H, s), |
| 43 (CF₃COOH salt) | Ar with OCOCH₃, OCOCH₃, H₃CO substituents | Pyrimidine with COOH, CH₃, -S- linkage; double bond | — 1 1 0 double bond | O | 1773, 1597, 1508, 1203, 1180. | (DMSO-d₆); 10.0(1H, d, J=7Hz), 7.6(1H, s), 7.4(1H, s), 7.2(1H, s), 7.1(1H, s), 5.8(1H, dd, J=4, 7Hz), 5.2(1H, d, J=4Hz), 4.4(2H, brs), 3.8(3H, s), 3.7(2H, ABq), 2.6(3H, s), 2.26(3H, s) 2.22(3H, s) |
| 44 (CF₃COOH salt) | Ar with OCOCH₂Cl, OCOCH₂Cl, CH₃ substituents | Pyrimidine with COOH, CH₃, -S- linkage; double bond | — 1 1 0 double bond | O | 1779, 1683, 1635, 1598, 1510, 1243, 1209, 1117. | (DMSO-d₆); 10.1(1H, d, J=8Hz), 7.9(1H, d, J=9Hz), 7.41(1H, s), 7.36(1H, d, J=9Hz), 7.2(1H, s), 5.9(1H, dd, J=5, 8Hz), 5.2(1H, d, J=5Hz), 4.9(2H, s), 4.7(2H, s), 4.4(2H, brs), 3.6(2H, ABq), 2.6(3H, s), 2.4(3H, s), |

TABLE 5-continued

TABLE 5-continued

| | Structure (phenol) | Structure (pyrazole) | | | | IR / NMR |
|---|---|---|---|---|---|---|
| 45 | 3-methyl catechol (OH, OH, CH3) | COOH-pyrazolo-pyrimidine with CH3, S- | O | — | 1 1 0 | double bond | 1778, 1773, 1735, 1637, 1597, 1509, 1302, 1245. | (DMSO—d6); 10.1(1H, d, J=8Hz), 7.42(1H, s), 7.37(1H, d, J=10Hz), 7.1(1H, s), 6.8(1H, d, J=10Hz), 5.9(1H, dd, J=5, 8Hz), 5.2(1H, d, J=5Hz), 4.5(2H, brs), 3.7(2H, ABq), 2.6(3H, s), 2.4(3H, s) |
| 46 (CF3COOH salt) | 6,7-bis(OCOCH3) naphthalene | same pyrazolo-pyrimidine | O | — | 1 1 0 | double bond | 1772, 1764, 1735, 1636, 1597, 1509, 1239, 1203. | (DMSO—d6); 10.1(1H, d, J=9Hz), 8.7(1H, s), 8.1(1H, s), 8.0(1H, s), 7.4(1H, s), 7.1(1H, s), 6.0(1H, dd, J=5, 9Hz), 5.3(1H, d, J=5 Hz), 4.4(2H, brs), 3.7(2H, ABq), 2.6(3H, s), 2.4(6H, s), |
| 47 | 4-methyl-1,2-dihydroxy naphthalene | same pyrazolo-pyrimidine | O | — | 1 1 0 | double bond | 1774, 1763, 1719, 1654, 1597, 1509, 1220, 1165, 1133. | (DMSO—d6); 10.1(1H, d, J=9Hz), 8.7(1H, m), 8.2(2H, m), 7.8(2H, m), 7.4(1H, s), 7.2(1H, s), 5.9(1H, dd, J=5, 9Hz), 5.2(1H, d, J=5 Hz), 4.4(2H, brs), 3.6(2H, ABq), 2.6(3H, s) |
| 48 (CF3COOH salt) | bis(OCOCH2Cl), methyl, isopropyl benzene | same pyrazolo-pyrimidine | O | — | 1 1 0 | double bond | 1773, 1595, 1508, | (DMSO—d6); 10.1(1H, d, J=9Hz), 7.7(1H, s), 7.5(1H, s), 7.4(1H, s), 7.1(1H, s), 5.8(1H, dd, J=5, 9Hz), 5.2(1H, d, J=5Hz), 4.7(2H, s), 4.6(2H, s), 4.4(2H, s), 3.6(2H, brs), 3.5(1H, m), 2.6(3H, s), 1.2–1.0(6H, s) |

| | | | | |
|---|---|---|---|---|
| 49 | phenol structure: 2-OH, 1-OH, 5-isopropyl, methyl | pyrazole-COOH with S-linked pyrimidine (CH₃) | O | — 1 1 0 double bond | 1773, 1741, 1654, 1630, 1597, 1515, 1509 | (DMSO—d₆); 10.0(1H, d, J=9Hz), 7.4(1H, s), 7.2(1H, s), 7.1(1H, s), 6.8(1H, s), 5.9(1H, dd, J=5, 9Hz), 5.2(1H, d, J=5Hz), 4.4(2H, brs), 3.7(1H, m), 2.6(3H, s), 1.1(6H, d, J=7 Hz) |
| 50 | phenol structure: OH, OH, Cl | pyrazole-COOH with S-linked pyrimidine (CH₃) | O | — 1 1 0 double bond | 1772, 1764, 1753, 1637, 1597, 1512, 1208 | (DMSO—d₆); 10.0(1H, d, J=9Hz), 7.4(1H, s), 7.3(1H, s), 7.1(1H, s), 6.9(1H, s), 5.8(1H, dd, J=5, 9Hz), 5.2(1H, d, J=5Hz), 4.4(2H, brs), 3.6(2H, ABq), 2.6(3H, s) |
| 51 (CF₃COOH salt) | phenol structure: OCOCH₃, OCOCH₃, isopropyl | pyrazole-COOH with S-linked pyrimidine (CH₃) | O | — 1 1 0 double bond | 1778, 1774, 1764, 1736, 1509, 1204, 1141 | (DMSO—d₆); 10.1(1H, d, J=8Hz), 7.6(1H, s), 7.42(1H, s), 7.39(1H, s), 7.1(1H, s), 5.9(1H, dd, J=5, 8Hz), 5.2(1H, d, J=5Hz), 4.4(2H, brs), 3.7(2H, ABq), 3.6(1H, m), 2.6(3H, s), 2.26(3H, s), 2.24(3H, s), 1.2(3H, d, J=5 Hz), 1.1(3H, d, J=5Hz) |
| 52 (CF₃COOH salt) | phenol structure: OCOCH₃, OCOCH₃, OCOCH₃, H₃C | pyrazole-COOH with S-linked pyrimidine (CH₃) | O | — 1 1 0 double bond | 1775, 1676, 1637, 1597, 1509, 1374, 1316, 1199, 1144 | (DMSO—d₆); 10.1(1H, d, J=9Hz), 7.7(1H, s), 7.4(1H, s), 7.1(1H, d, J=5Hz), 5.8(1H, dd, J=5, 9 Hz), 5.2(1H, d, J=5Hz), 4.4(2H, brs), 3.7(2H, ABq), 2.6(3H, s), 2.4(3H, s), 2.36(6H, s), 2.2(3H, s) |

TABLE 5-continued

| | | | | | | |
|---|---|---|---|---|---|---|
| 53 (CF$_3$COOH salt) | ![structure with NH$_2$ groups on tolyl] | ![pyrazolo-pyrimidine structure with COOH, CH$_3$, S-] | O | — | 1 1 0 double bond | 1775, 1735, 1676, 1634, 1599, 1508, 1262, 1202. | (DMSO—d$_6$); 10.0(1H, d, J=8Hz), 7.6–6.7(5H, m), 6.0(1H, dd, J=5, 8Hz), 5.3(1H, d, J=5 Hz), 4.4(2H, brs), 3.7(2H, ABq), 2.6(3H, s) |
| 54 (CF$_3$COOH salt) | ![structure with NHCO$_2$CH$_2$C$_6$H$_5$ groups] | ![pyrazolo-pyrimidine structure with COOH, CH$_3$, S-] | O | — | 1 1 0 double bond | 1780, 1773, 1730, 1617, 1597, 1509, 1219, 1199. | (DMSO—d$_6$); 10.2(1H, d, J=8Hz), 9.3(1H, s), 9.2(1H, s), 8.3–7.1(15H, m), 5.9(1H, dd, J=5, 8Hz), 5.3(1H, d, J=5Hz), 5.2(4H, s), 4.4(2H, brs), 3.7(2H, ABq), 2.6(3H, s) |
| 55 | ![structure with OH, OH, H$_3$C on phenyl] | ![pyrazolo-pyrimidine structure with SO$_3$H, CH$_3$, S-] | O | — | 1 1 0 double bond | 1773, 1654, 1595, 1509, 1369. | (DMSO—d$_6$); 10.0(1H, d, J=8Hz), 7.4(1H, s), 7.3(1H, s), 7.1(1H, s), 6.7(1H, s), 5.9(1H, dd, J=5, 8Hz), 5.2(1H, d, J=5Hz), 4.4(2H, brs), 3.6(2H, ABq), 2.6(3H, s), 2.4(3H, s) |
| 56 (CF$_3$COOH salt) | H | ![pyrimidine structure with OH, COOH, N-N, S-] | — | — | 1 0 0 double bond | 1773, 1695, 1647, 1588, 1542. | (DMSO—d$_6$); 11.9(1H, s), 9.6(1H, d, J=9Hz), 8.6(1H, s), 6.8(1H, s), 5.8(1H, dd, J=5, 9 Hz), 5.2(1H, d, J=5Hz), 4.3(2H, ABq), 3.7 (2H, ABq) |

TABLE 5-continued

| No. | Structure | R | X | a | b | c | d | IR | NMR |
|---|---|---|---|---|---|---|---|---|---|
| 57 (CF₃COOH salt) | ![structure with imidazo-pyrimidine-COOH] | H | — | — | — | 1 0 0 | double bond | 1774, 1684, 1630, 1541, 1370, 1187. | (DMSO—d₆); 11.3(1H, s), 9.4(1H, d, J=8Hz), 8.5(1H, s), 7.5(1H, s), 6.6(1H, s), 5.8(1H, dd, J=5, 8Hz), 5.1(1H, d, J=5Hz), 4.4(2H, ABq), 3.7(2H, ABq) |
| 58 (CF₃COOH salt) | ![structure with imidazo-pyrimidine-CH₃] | OH | H | O | 1 1 1 | double bond | | 1775, 1595, 1515, 1355, 1255, 1195, 1080. | (DMSO—d₆); 9.5(1H, d, J=9Hz), 8.6(1H, s), 7.3(1H, s), 6.8(1H, s), 5.8(1H, dd, J=5, 9 Hz), 5.2(1H, d, J=5Hz), 4.6(2H, s), 4.4(2H, brs), 3.7(2H, ABq), 2.6(3H, s) |
| 59 (CF₃COOH salt) | ![structure with imidazo-pyrimidine-COOH-CH₃] | OH | H | O | 1 1 1 | double bond | | 1774, 1630, 1595, 1505, 1400, 1240. | (DMSO—d₆); 9.5(1H, d, J=9Hz), 7.4(1H, s), 6.8(1H, s), 5.8(1H, dd, J=5, 9Hz), 5.2(1H, d, J=5Hz), 4.6(2H, s), 4.4(2H, s), 3.7(2H, ABq), 2.6(3H, s) |
| 60 (CF₃COOH salt) | ![structure with imidazo-pyrimidine-CH₃] | OH | CH₃ | CH₃ | O | 1 1 1 | double bond | 1775, 1675, 1630, 1595, 1515, 1360, 1190. | (DMSO—d₆); 9.5(1H, d, J=9Hz), 8.6(1H, s), 7.3(1H, s), 6.7(1H, s), 5.8(1H, dd, J=5, 9 Hz), 5.2(1H, d, J=5Hz), 4.4(2H, s), 3.7(2H, ABq), 2.6(3H, s), 1.4(6H, s) |

TABLE 5-continued

| No. | Structure 1 | Structure 2 | R1 | R2 | R3 | R4 | Bond | IR | NMR |
|---|---|---|---|---|---|---|---|---|---|
| 61 (CF3COOH salt) | phenol with OH and CH3 | pyrazolo-pyrimidine COOH/CH3/S | H | H | — | — | 1 1 0 double bond | 1780, 1683, 1637, 1599, 1509, 1198. | (DMSO-d6); 9.8(1H, d, J=8Hz), 7.4-6.7(5H, m), 5.8(1H, dd, J=5, 8Hz), 5.2(1H, d, J=5 Hz), 4.9(2H, brs), 4.4(2H, brs), 3.7(2H, ABq), 2.6(3H, s) |
| 62 (CF3COOH salt) | phenol with COOCH3 and COOCH3 | pyrazolo-pyrimidine COOH/CH3/S | H | H | O | — | 1 1 1 double bond | 1774, 1685, 1596, 1509, 1202. | (DMSO-d6); 9.8(1H, d, J=8Hz), 8.0-7.4(4H, m), 6.8(1H, s), 5.9(1H, dd, J=5, 8Hz), 5.4 (2H, s), 5.2(1H, d, J=5Hz), 4.4(2H, brs), 3.6(2H, ABq), 2.6(3H, s), 2.3(6H, s) |
| 63 (CF3COOH salt) | aminophenol with OH | pyrazolo-pyrimidine COOH/CH3/S | CH3 | CH3 | O | — | 1 1 1 double bond | 1774, 1683, 1597, 1512. | (DMSO-d6); 9.9(1H, d, J=8Hz), 8.7(1H, s), 7.4(1H, s), 7.1-6.6(4H, m), 5.9(1H, dd, J=5, 8Hz), 5.3(1H, d, J=5Hz), 4.4(2H, brs), 3.7(2H, ABq), 2.6(3H, s), 1.5(6H, s) |
| 64 (CF3COOH salt) | bis(tolyl-OSO2) diphenyl | pyrazolo-pyrimidine COOH/CH3/S | — | — | — | — | 1 0 0 double bond | 1784, 1685, 1676, 1637, 1598, 1509, 1491, 1375, 1195, 1180. | (DMSO-d6); 9.9(1H, d, J=8Hz), 7.6-7.0(13H, m), 5.9(1H, dd, J=5, 8Hz), 5.3(1H, d, J=5 Hz), 4.4(2H, brs), 3.7(2H, s), 2.6(3H, s), 2.41(3H, s)2.38(3H, s) |

TABLE 5-continued

| | | | | | | | | | |
|---|---|---|---|---|---|---|---|---|---|
| 65 (CF₃COOH salt) | ![aryl: pyridine-like ring with CH₂N, COOCH₃, OH] | ![heterocycle: COOH-N=N ring fused, CH₃, S-link] | CH₃ | CH₃ | O | 1 | 1 | 1 | double bond | 1781, 1774, 1676, 1671, 1637, 1196, 1143. | (DMSO—d6); 9.6 and 9.5(1H, m), 7.4(1H, s), 7.2 (3H, s), 6.84 and 6.81(1H, s), 5.8(1H, m), 5.2 (1H, d, J=4Hz), 4.8(1H, m), 4.4(2H, brs), 3.7(2H, ABq), 3.2(2H, m), 2.6(3H, s), 2.2(6H, s) |
| 66 (CF₃COOH salt) | ![aryl: benzene with two COOCH₃] | ![heterocycle] | H | COOH | H | H | 1 | 1 | 1 | double bond | 1772, 1735, 1684, 1637, 1597, 1509, 1259, 1205, 1189. | (DMSO—d6); 9.6(1H, d, J=8Hz), 8.0(1H, s), 7.4(2H, s), 6.8(1H, s), 5.9(1H, dd, J=4, 8 Hz), 5.3(1H, d, J=4Hz), 4.4(2H, brs), 3.7 (2H, ABq), 2.6(3H, s), 2.3(3H, s), 1.6(6H, s) |
| 67 (Na salt) | ![aryl: catechol] | ![heterocycle] | H | COOH | H | H | 1 | 1 | 1 | double bond | 1765, 1597, 1516, 1474, 1408, 1356, 1314. | (D₂O); 7.4 and 7.2(1H, s), 7.0(1H, s), 6.8– 6.6(3H, s), 5.7(1H, m), 5.2(1H, m), 5.0(1H, m), 4.5(2H, ABq), 3.7(2H, ABq), 3.0(2H, m), 2.6 (3H, s) |
| 68 (CF₃COOH salt) | ![aryl: benzene with two COOCH₃, CH₃] | ![heterocycle] | H | H | — | — | 1 | 1 | 0 | double bond | 1772, 1741, 1654. | (DMSO—d6); 9.4(1H, d, J=8Hz), 7.4(1H, s), 7.3(1H, s), 7.0(1H, s), 6.8(1H, s), 5.8(1H, dd, J=4, 8Hz), 5.7(1H, s), 5.1(1H, d, J=4 Hz), 4.4(2H, brs), 3.6(2H, ABq), 2.6(3H, s), 2.43(3H, s), 2.2(6H, s) |

TABLE 5-continued

| No. | Ar | R[1] | R[2] | 1-10 bond | IR | NMR |
|---|---|---|---|---|---|---|
| 69 (Na salt) | 2,4-dihydroxy-5-methylphenyl (OH, OH, H₃C substituted phenyl) | H | COOH | 1—1 0 double bond | 1770, 1597, 1513, 1407, 1384, 1311. | (D₂O); 7.3–6.6(4H, m), 5.63–5.59(2H, m), 5.01–4.95(1H, m), 4.8–4.4(2H, m), 3.6–3.0 (2H, m), 2.6(3H, s), 2.23 and 2.17(3H, s) |
| 70 (CF₃COOH salt) | 2,3-dihydroxy-methylphenyl (OH, OH substituted phenyl with CH₃ implied) | H | COOH | 1—1 0 double bond | 1774, 1676, 1637, 1597, 1511, 1198. | (DMSO—d₆); 9.5(1H, m), 7.4(1H, m), 6.84 and 6.81(1H, s), 6.7(3H, m), 5.96 and 5.91(1H, s), 5.8(1H, m), 5.2(1H, d, J=5Hz), 4.4(2H, brs), 3.7(2H, ABq), 2.6(3H, s) |
| 71 (CF₃COOH salt) | phenyl | H | COOH | 1—1 0 double bond | 1778, 1722, 1675, 1636, 1597, 1509, 1200. | (DMSO—d₆); 9.5(1H, m), 7.5–7.0(6H, m), 6.83 and 6.80(1H, s), 5.8(1H, m), 5.6(1H, s), 5.2 (1H, m), 4.4(2H, brs), 3.7(2H, ABq), 2.6(3H, s) |
| 72 (CF₃COOH salt) | 4-(methoxycarbonyl)phenyl (COOCH₃ substituted phenyl) | H | COOH | 1—1 0 double bond | 1773, 1735, 1675, 1509, 1202. | (DMSO—d₆); 9.5(1H, m), 7.6–7.1(5H, m), 6.83 and 6.79(1H, s), 5.6(1H, m), 5.6(1H, s), 5.1 (1H, m), 4.4(2H, trs), 3.6(2H, ABq), 2.6(3H, s), 2.25 and 2.20(3H, s) |

Common core structure for compounds 69–72:

Pyrazolo-pyrimidine system bearing COOH, with N—N ring, CH₃ substituent, and —S— linker to Ar group.

TABLE 5-continued

| | | | | 1 | 1 | 0 | | | |
|---|---|---|---|---|---|---|---|---|---|
| 73 (Na salt) | *4-hydroxyphenyl* | *COOH-substituted imidazopyrimidine with CH3 and S* | H | COOH | — | — | 1 1 0 | double bond | 1762, 1654, 1616, 1598, 1406. | (D$_2$O); 7.5–6.8(6H, m), 5.7(1H, m), 5.5(1H, s), 5.0(1H, m), 4.4(2H, ABq), 3.4(2H, ABq), 2.6(3H, s) |
| 74 (Na salt) | *3-hydroxy-4-methylphenyl* | —COOCH$_3$ | H | COOH | — | — | 1 1 0 | double bond | 1772, 1762, 1751, 1617, 1399. | (D$_2$O); 7.0–6.9(4H, m), 5.8(1H, m), 5.4(1H, s), 3.4(2H, ABq), 2.1(3H, s) |
| 75 (Na salt) | *3-hydroxy-4-methylphenyl* | *thiadiazole-S* | H | COOH | — | — | 1 1 0 | double bond | 1773, 1597, 1529, 1390, 1358. | (D$_2$O); 8.7(1H, s), 7.0–6.8(4H, m), 5.7(1H, m), 5.4(1H, s), 5.0(1H, s), 4.3(2H, ABq), 3.3 (2H, ABq) |
| 76 (Na salt) | *3-hydroxy-4-methylphenyl* | *SO$_3$Na-substituted imidazopyrimidine with CH$_3$ and S* | H | COOH | — | — | 1 1 0 | double bond | 1763, 1596, 1509, 1397, 1368. | (D$_2$O); 7.2(1H, s), 7.0–6.9(4H, m), 5.7(1H, m), 5.4(1H, s), 5.0(1H, m), 4.3(2H, ABq), 3.4 (2H, ABq), 2.6(3H, s) |
| 77 (Na salt) | *3-hydroxy-4-methylphenyl* | *imidazopyrimidine with CH$_3$ and S* | H | COOH | — | — | 1 1 0 | double bond | 1763, 1596, 1513, 1399, 1205. | (D$_2$O); 8.5 and 8.3 (1H, s), 7.2–6.8(5H, m), 5.6(1H, m), 5.4(1H, s), 5.0(1H, m), 3.4(2H, ABq), 2.6 and 2.4(2H, s) |

TABLE 5-continued

| | | | | | |
|---|---|---|---|---|---|
| 78 (Na salt) | [catechol-methyl] | H | COOH | — — 110 double bond | 1763, 1612, 1533, 1475, 1396. | ($D_2O$); 8.4(1H, s), 7.3(1H, s), 7.0-6.9(4H, m), 5.7(1H, m), 5.4(1H, s), 5.0(1H, m), 4.3(2H, ABq), 3.4(2H, ABq), 2.6(3H, s) |
| 79 (Na salt) | [catechol-methyl] | H | COOH | — — 110 double bond | 1763, 1617, 1534, 1458, 1397, 1368, 1318. | ($D_2O$); 7.4(1H, s), 7.0-6.9(4H, m), 5.7(1H, m), 5.4(1H, s), 5.0(1H, m), 4.3(2H, ABq), 3.4(2H, ABq), 2.6(3H, s) |
| 80 (Na salt) | [catechol-methyl] | H | COOH | — — 110 double bond | 1763, 1597, 1523, 1396. | ($D_2O$); 8.6(1H, s), 7.0-6.8(4H, m), 5.6(1H, m), 5.4(1H, s), 3.4(2H, ABq) |
| 81 (Na salt) | [catechol-methyl] | H | COOH | — — 110 double bond | 1773, 1637, 1560, 1400. | ($D_2O$); 7.0-6.9(4H, m), 5.6(1H, m), 5.4(1H, s), 5.1(1H, s), 4.0(3H, s), 3.4(2H, ABq) |
| 82 (Na salt) | [catechol-methyl] | H | COOH | — — 110 double bond | 1772, 1610, 1508, 1384. | ($D_2O$); 7.0-6.9(4H, m), 5.7(1H, m), 5.4(1H, s), 5.0(2H, s), 4.2(2H, ABq), 3.4(2H, ABq) |
| 83 (Na salt) | [catechol-methyl] | H | COOH | — — 110 double bond | 1765, 1597, 1531, 1388. | ($D_2O$); 7.0-6.9(4H, m), 5.7(1H, m), 5.4(1H, m), 4.2(2H, ABq), 3.4(2H, ABq), 2.7(3H, s) |

TABLE 5-continued

| | | | | | | IR | NMR |
|---|---|---|---|---|---|---|---|
| 84 (Na salt) | 3-OH, 4-CH₃ phenyl | [structure: pyrimidinone with CH₃, O, N, N, S] | H | COOH | — | — | 1 1 0 double bond | 1763, 1598, 1533, 1396. | (D₂O); 7.0-6.9(4H, m), 6.4(1H, s), 5.7(1H, m), 5.4(1H, s), 5.3(1H, m), 3.5(2H, ABq), 2.4 (3H, s) |
| 85 (Na salt) | 3-OH, 4-CH₃ phenyl | [structure: imidazo-pyrimidine with COONa, S−] | H | COOH | — | — | 1 1 0 double bond | 1762, 1662, 1533, 1395. | (D₂O); 8.5(1H, s), 7.3(1H, s), 7.0-6.8(4H, m), 5.8(1H, m), 5.4(1H, s), 3.6(2H, ABq) |
| 86 (Na salt) | 3-OH, 4-CH₃ phenyl | [structure with CH₃, CH₂COONa, N, S] | H | COOH | — | — | 1 1 0 double bond | 1762, 1670, 1592, 1590, 1394. | (D₂O); 7.0-6.9(4H, m), 5.7(1H, m), 5.4(1H, s), 5.01 and 4.96(1H, s) |
| 87 (Na salt) | 3-OH, 4-CH₃ phenyl | [structure: imidazo-pyrimidine with CH₂COONa, S−] | H | COOH | — | — | 1 1 0 double bond | 1763, 1623, 1595, 1395. | (D₂O); 8.5(1H, s), 7.2(1H, s), 7.0-6.9(4H, m), 5.7(1H, m), 5.4(1H, s), 5.0(1H, m), 4.5 (2H, ABq), 3.5(2H, ABq), 2.6(2H, s) |
| 88 (Na salt) | 3-OH, 4-CH₃ phenyl | [structure: isothiazole with OH, NaOOC, N, S] | H | COOH | — | — | 1 1 0 double bond | 1752, 1596, 1528, 1395. | (D₂O); 7.0-6.9(4N, m), 5.6(1H, m), 5.4(1H, s), 5.0-5.1(1H, s), 3.8-3.3(4H, m) |

TABLE 5-continued

| No. | X | | R⁵ | a bond a | b | c | of ( ) | IR(cm⁻¹) | NMR (δ) |
|---|---|---|---|---|---|---|---|---|---|
| 89 (Na salt) | 2-OH, 5-CH₃ phenyl | COONa pyrimidine structure with -S-, N-N, OH | H COOH | — | — | 1 1 0 | double bond | 1762, 1624, 1598, 1396. | (D₂O); 7.0–6.9(4H, m), 6.2(1H, s), 5.7(1H, m), 5.4(1H, s), 3.3(2H, ABq) |
| 90 (CF₃COOH salt) | 2-COOCH₃, 3-COOCH₃, 5-CH₃ phenyl | COOH pyrimidine with -S-, N-N, CH₃ | O | — | — | 0 1 0 | single bond | 1774, 1654, 1647, 1509, 1205. | (DMSO–d₆); 9.2(1H, d), 8.9–8.8(1H, m), 7.9–7.3(4H, m), 6.6(1H, s), 5.8–5.6(2H, m), 5.1(1H, d, J=4 Hz), 4.4(2H, brs), 3.7(2H, ABq), 2.6(3H, s), 2.3(4H, s) |
| 91 (CF₃COOH salt) | 2-OCOCH₃, 3-OCOCH₃, 5-CH₃ phenyl | COOH pyrimidine with -S-, N-N, CH₃ | O | — | — | 0 1 0 | single bond | 1779, 1512, 1203, 1191. | (DMSO–d₆); 9.2(1H, d, J=8Hz), 8.8(1H, d, J=6 Hz), 7.8(2H, s), 7.4(1H, s), 6.6(1H, s), 5.8(1H, dd, J=5, 8 Hz), 5.6(1H, d, J=6 Hz), 5.1(1H, d, J=5 Hz), 4.4(2H, brs), 3.7(2H, ABq), 2.6(3H, s), 2.3(9H, s) |

| Example No. | X | R¹ | R² | R³ | R⁴ | R⁵ | a b c | a bond of ( ) | IR(cm⁻¹) | NMR (δ) |
|---|---|---|---|---|---|---|---|---|---|---|
| 92 | 2-OCOCH₃, 3-OCOCH₃, 5-CH₃ phenyl | (C₆H₅)₃C | CH₃ | COOCH(C₆H₅)₂ | — | — | 1 1 0 | double bond | 1773, 1751, 1743, 1262, 1209, 1168, 1115, 701. | (DMSO–d₆); 8.8(1H, s), 7.6–6.9(28H, m), 6.8(1H, s), 6.7(1H, s), 2.3(6H, s), 1.9(3H, s) |

TABLE 5-continued

| | | | | | | | |
|---|---|---|---|---|---|---|---|
| 93 | -N(H)- phenyl with OCH2O(CH2)2OCH3 and OCH2O(CH2)2OCH3 substituents | (C6H5)3C | CH3 | CH3 | 1 | 1 | 1 double bond | 1685, 1600, 1598, 1532, 1521, 1509, 1215, 1197, 1164, 1100, 702. | (DMSO—d6); 8.91(1H, s), 8.87(1H, s), 7.6–7.0 (18H, m), 6.9(1H, s), 5.2(4H, s), 3.6(8H, m), 3.22(3H, s), 3.21(3H, s), 1.5(6H, s) |
| 94 | phenyl with two OSO2-p-tolyl groups (CH3 para) | (C6H5)3C | — | — | 1 | 0 | 0 double bond | 1598, 1491, 1380, 1195, 1180, 1168, 1080, 850, 705. | (DMSO—d6); 8.9(1H, s), 7.7–6.9(27H, m), 2.4 (6H, s) |
| 95 | phenyl with OCOCH3 and OCOCH3 | (C6H5)3C | H | COOCH(C6H5)2 | H | 1 | 1 | 1 double bond | 1768, 1764, 1752, 1214, 1185, 701. | (DMSO—d6); 8.8(1H, s), 7.5–6.9(28H, m), 6.8 (2H, s), 5.0(1H, t, J=7 Hz), 3.2(2H, d, J=7 Hz), 2.2(6H, s) |
| 96 | phenyl (H3C substituent) with OCOCH3 and OCOCH3 | (C6H5)3C | H | COOCH(C6H5)2 | — | 1 | 1 | 0 double bond | 1772, 1764, 1210, 1181, 700. | (DMSO—d6); 8.9(1H, s), 7.4–7.0(27H, m), 6.9 (2H, s), 6.0(1H, s), 2.3 (9H, s) |
| 97 | phenyl with OH and OH | (C6H5)3C | H | COOCH(C6H5)2 | — | 1 | 1 | 0 double bond | 1734, 1624, 1595, 1491, 1478, 1285, 1183, 700. | (DMSO—d6); 9.6(1H, s), 8.91(1H, s), 8.86(1H, s), 7.6–7.0(27H, m), 6.8(2H, s), 6.6(1H, s), 6.1(1H, s) |
| 98 | phenyl | (C6H5)3C | H | COOCH(C6H5)2 | — | 1 | 1 | 0 double bond | 1741, 1542, 1496, 1449, 1253, 1182, 659. | (CDCl3); 7.6–6.9(31H, m), 6.9(1H, s), 6.8(1H, s), 6.0(1H, s) |
| 99 | phenyl with OCOCH3 | (C6H5)3C | H | COOCH(C6H5)2 | — | 1 | 1 | 0 double bond | 1761, 1758, 1751, 1745, 1540, 1533, 1507, 1496, 1202, 1167. | (DMSO—d6); 8.9(1H, s), 7.5–6.9(29H, m), 6.85 (1H, s), 6.82(1H, s), 5.9(1H, s), 2.3(3H, s) |

The following examples detail typical pharmaceutical preparations containing the cephalosporin derivatives of the present invention. These examples are not intended to limit the types of compounds to be used, but the methods are applicable to all the compounds of the present invention.

EXAMPLE A (Method of manufacturing f:freeze-dried-dried parenteral injections)

(6R,7R)-7-[2-(2-amino-4-thiazolyl)-2-[Z-carboxy-[(3,4-dihydroxyphenyl)methyl]imino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (1.1 g) was dissolved in 22 ml of sterile water containing an equivalent amount of sodium bicarbonate, and 2 ml each of this solution was poured into 5-ml ampoules, freeze-dried and sealed by ordinary methods, to produce a freeze-dried preparation for parenteral injections.

EXAMPLE B (Method of manufacturing tablet for oral administration) Granules were prepared by ordinary methods using 50 mg of (6R,7R)-7-[2-(2-amino-4-thiazolyl -2-[Z-(4,5-diacetoxy-2-methylbenzoyl)oxyimino)acetamido]-3-[(2-carboxy-5-methyl-s-triazolo[1,5-a]pyrimidin-7-yl)thiomethyl]-8-oxo-5-thia-1-azabicyclo[4.2.0]-oct-2-ene-2-carboxylic acid, 100 mg of lactose, 30 mg of starch, and 10 mg of polyvinyl pyrrolidone. Starch (30 mg) and magnesium stearate (5 mg) were further added to the granules, and the resulting mixture was compressed into tablets, each piece weighing 425 g.

EXAMPLE C (Method of manufacturing gelatin capsules for oral administration)

(6R,7R)-7-[2-(2-amino-4-thiazolyl)-2-[Z.(4,5-dihydroxy-2-methylbenzoyl]oxyimino]acetamido]-3-[(2-carboxyl-5-methyl-s-triazolo[1,5-a]pyrimidin-7-yl)thiomethyl]-8-oxo-5-thia-1-azabicyclo[4.2.0 oct-2-ene-2-carboxylic acid (250 mg), water-soluble polyvinyl pyrrolidone (15 mg), mannitol (15 mg), talc (15 mg) and magnesium stearate (5 mg) were uniformly mixed, and filled into gelatin capsules each weighing 300 mg.

What is claimed is:

1. A cephalosporin derivative represented by the formula (XIV):

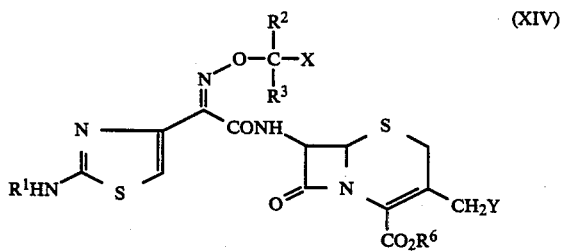
(XIV)

or pharmacuetically or veterinarily acceptable non-toxic salts or solvates or non-toxic salts of solvates thereof: wherein $R^1$ represents a hydrogen atom or an amino-protecting group, no represents a hydrogen atom, a methyl group, a carboxyl group, or protected carboxyl group, $R^3$ represents a hydrogen atom or a ethyl group, $R^6$ represents a hydrogen atom or a carboxy protecting group, X represents a group:

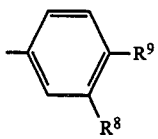

wherein $R^8$ and $R^9$ are the same or different and represent hydroxy groups or acetoxy groups, and Y represents a group:

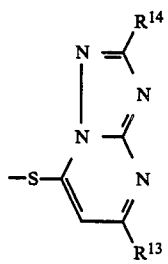

wherein $R^{13}$ represents a methyl group and $R^{14}$ represents a carboxyl group or a protected carboxyl group.

2. A cephalosporin derivative as claimed in claim 1, wherein $R^1$ and $R^6$ each represent a hydrogen atom.

3. A cephalosporin derivative as claimed in claim 2, wherein $R^2$ represents a carboxyl group or a protected carboxyl group.

4. A cephalosporin derivative as claimed in claim 2, wherein $R^2$ represents a carboxyl group, $R^3$ represents a hydrogen atom, $R^8$ and $R^9$ represent hydroxy groups, $R^{13}$ represents a methyl group, and $R^{14}$ represents a carboxyl group.

5. A cephalosporin derivative as claimed in claim 3, wherein the absolute configuration of the carbon atom to which $R^2$ and $R^3$ are connected is (S)-configuration.

6. A cephalosporin derivative as claimed in claim 4, wherein the absolute configuration of the carbon atom to which $R^2$ and $R^3$ are connected is (S)-configuration.

7. An antibiotic pharmaceutical or antibiotic veterinary composition which comprises a pharmacuetically or veterinarily acceptable carrier and a pharmaceutically or veterinarily effective amount of at east one member selected from group consisting of cephalosporin derivatives represented by the formula (XIV):

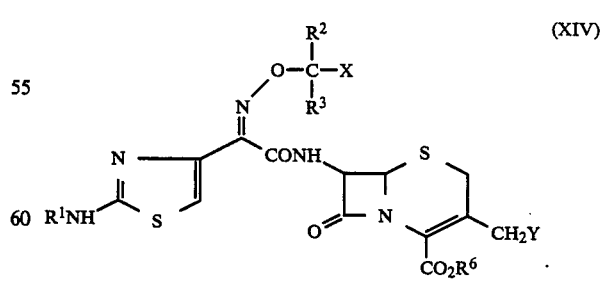
(XIV)

non-toxic salts, solvates and non-toxic salts of solvates thereof; wherein $R^1$ represents a hydrogen atom or an amino-protecting group, $R^2$ represents a hydrogen atom, a methyl group, a carboxyl group, or a protected carboxyl group, $R^3$ represents a hydrogen atom or a methyl group, $R^6$ represents a hydrogen atom or a carboxy protecting group, X represents a group:

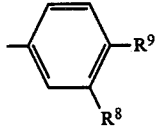

wherein $R^8$ and $R^9$ are the same or different and represent hydroxy groups or acetoxy groups, and Y represents a group:

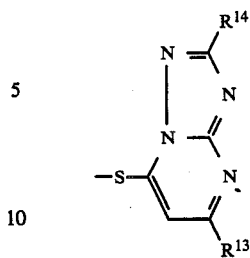

wherein $R^{12}$ represents a methyl group and $R^{14}$ represents a carboxyl group or a protected carboxyl group.

8. A composition as claimed in claim 7, wherein $R^1$ and $R^6$ each represent a hydrogen atom.

9. A composition as claimed in claim 8, wherein $R^2$ represents a carboxyl group or a protected carboxyl group.

10. A composition as claimed in claim 8, wherein $R^2$ represents a carboxyl group, $R^3$ represents a hydrogen atom, $R^8$ and $R^9$ represent hydroxy groups, and $R^{14}$ represents a carboxyl group.

11. A composition as claimed in claim 9, wherein the absolute configuration of the carbon atom to which $R^2$ and $R^3$ are connected is (S)-configuration.

12. A composition as claimed in claim 10, wherein the absolute configuration of the carbon atom to which $R^2$ and $R^3$ are connected is (S)-configuration.

* * * * *

UNITED STATES PATENT AND TRADEMARK OFFICE
CERTIFICATE OF CORRECTION

PATENT NO. : 4,840,945
DATED : June 20, 1989
INVENTOR(S) : Haruo OHNISHI et al

It is certified that error appears in the above-identified patent and that said Letters Patent is hereby corrected as shown below:

Claim 1, column 81, line 66, change "no" to --$R^2$--;

column 82, line 1, change "ethyl" to --methyl--.

Claim 7, column 82, line 48, change "east" to --least--;

column 84, line 13, change "$R^{12}$" to --$R^{13}$--.

Signed and Sealed this

Twenty-sixth Day of June, 1990

Attest:

HARRY F. MANBECK, JR.

*Attesting Officer*   *Commissioner of Patents and Trademarks*